United States Patent
Estes

(10) Patent No.: US 9,901,677 B2
(45) Date of Patent: Feb. 27, 2018

(54) INFUSION PUMP SYSTEM AND METHODS

(71) Applicant: Bigfoot Biomedical, Inc., Milpitas, CA (US)

(72) Inventor: Mark C. Estes, Malibu, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 898 days.

(21) Appl. No.: 13/652,905

(22) Filed: Oct. 16, 2012

(65) Prior Publication Data
US 2014/0107607 A1  Apr. 17, 2014

(51) Int. Cl.
| | |
|---|---|
| *A61K 9/22* | (2006.01) |
| *A61M 5/168* | (2006.01) |
| *A61M 5/145* | (2006.01) |
| *A61M 5/172* | (2006.01) |
| *A61M 5/50* | (2006.01) |
| *A61M 5/142* | (2006.01) |
| *G06F 19/00* | (2018.01) |

(52) U.S. Cl.
CPC ...... *A61M 5/16831* (2013.01); *A61M 5/1452* (2013.01); *A61M 5/14244* (2013.01); *A61M 5/1723* (2013.01); *A61M 5/50* (2013.01); *G06F 19/3468* (2013.01); *A61M 2205/27* (2013.01); *A61M 2205/3569* (2013.01); *A61M 2205/502* (2013.01)

(58) Field of Classification Search
CPC ...... A61M 5/142; A61M 5/172; A61M 5/168; A61M 5/14244; A61M 5/14248; A61M 5/1723; A61M 2005/14264; A61M 2005/1726; G06F 19/3468
USPC .............................................. 604/131, 66, 67
See application file for complete search history.

(56) References Cited

U.S. PATENT DOCUMENTS

| | | | |
|---|---|---|---|
| 5,822,715 A * | 10/1998 | Worthington et al. ......... 702/19 |
| 5,984,894 A | 11/1999 | Poulsen |
| 6,551,276 B1 | 4/2003 | Mann et al. |
| 6,554,798 B1 | 4/2003 | Mann et al. |
| 6,659,978 B1 | 12/2003 | Kasuga |
| 6,691,043 B2 | 2/2004 | Ribeiro, Jr. |
| 6,744,350 B2 | 6/2004 | Blomquist |
| 6,852,104 B2 | 2/2005 | Blomquist |
| 6,925,393 B1 | 8/2005 | Kalatz et al. |

(Continued)

FOREIGN PATENT DOCUMENTS

| | | |
|---|---|---|
| EP | 0 062 974 A1 | 10/1982 |
| EP | 0 275 213 A2 | 7/1988 |

(Continued)

OTHER PUBLICATIONS

"Using the Deltec Cozmo Insulin Pump Correction Bolus Feature" believed to be publicly available before May 5, 2008, pp. 36-41.

(Continued)

*Primary Examiner* — Kevin C Sirmons
*Assistant Examiner* — Leah Swanson
(74) *Attorney, Agent, or Firm* — Fish & Richardson P.C.

(57) ABSTRACT

Some embodiments an infusion pump system can be configured to activate an alarm in response to a calculated prediction of the user's future blood glucose levels. Optionally, the predictive calculation of the user's future blood glucose levels can be based at least in part upon a recent blood glucose level, a trend of blood glucose levels over time, and an insulin load of the user.

23 Claims, 10 Drawing Sheets

(56) References Cited

U.S. PATENT DOCUMENTS

| | | | |
|---|---|---|---|
| 6,936,029 | B2 | 8/2005 | Mann et al. |
| 6,979,326 | B2 | 12/2005 | Mann et al. |
| 6,997,920 | B2 | 2/2006 | Mann et al. |
| 7,025,743 | B2 | 4/2006 | Mann et al. |
| 7,109,878 | B2 | 9/2006 | Mann et al. |
| 7,278,983 | B2 | 10/2007 | Ireland et al. |
| 7,547,281 | B2 * | 6/2009 | Hayes et al. ............... 600/365 |
| 7,704,226 | B2 | 4/2010 | Mueller, Jr. et al. |
| 8,029,459 | B2 | 10/2011 | Rush et al. |
| 2003/0114836 | A1 * | 6/2003 | Estes ................ A61M 5/14244 604/890.1 |
| 2004/0167464 | A1 | 8/2004 | Ireland et al. |
| 2004/0176720 | A1 | 9/2004 | Kipfer |
| 2006/0173406 | A1 | 8/2006 | Hayes et al. |
| 2007/0073228 | A1 | 3/2007 | Mernoe et al. |
| 2007/0073235 | A1 | 3/2007 | Estes et al. |
| 2007/0073236 | A1 | 3/2007 | Mernoe et al. |
| 2007/0118405 | A1 | 5/2007 | Campbell et al. |
| 2007/0167912 | A1 | 7/2007 | Causey et al. |
| 2007/0173761 | A1 | 7/2007 | Kanderian, Jr. et al. |
| 2007/0179444 | A1 | 8/2007 | Causey et al. |
| 2008/0125700 | A1 | 5/2008 | Moberg et al. |
| 2008/0201325 | A1 * | 8/2008 | Doniger et al. ................ 707/5 |
| 2008/0294094 | A1 | 11/2008 | Mhatre et al. |
| 2008/0294142 | A1 | 11/2008 | Patel et al. |
| 2010/0094251 | A1 | 4/2010 | Estes |
| 2010/0298765 | A1 * | 11/2010 | Budiman et al. ............... 604/66 |
| 2011/0040247 | A1 * | 2/2011 | Mandro ................ A61M 5/142 604/66 |
| 2012/0123234 | A1 * | 5/2012 | Atlas .................... A61B 5/7264 600/365 |
| 2012/0249294 | A1 * | 10/2012 | O'Connor ........... A61M 5/1723 340/5.53 |
| 2012/0259278 | A1 | 10/2012 | Hayes et al. |

FOREIGN PATENT DOCUMENTS

| | | |
|---|---|---|
| EP | 1 045 146 A2 | 12/2000 |
| EP | 1 818 664 A | 8/2007 |
| WO | WO 2004/056412 A2 | 7/2004 |
| WO | WO 2004/110526 A | 12/2004 |

OTHER PUBLICATIONS

"Which Insulin Pump is Right for Me?", Albany Medical Center, Goodman Diabetes Service, Jan. 2006, 4 pages.

Brown et al., "CGM, Pumps, and SMBG." American Diabetes Association—71st Scientific Sessions, San Diego, CA, Jun. 24-28, 2011, 38 pages.

Cox et al. "Prediction of Severe Hypoglycemia." *Diabetes Care*, vol. 30, No. 6, Jun. 2007, 4 pages.

*The Content of Investigational Device Exemption (IDE) and Premarket Approval (PMA) Application for Low Glucose Suspend (LGS) Device System*. Rockville, MD, Food and Drug Administration, 2011, 59 pages.

International Search Report and Written Opinion in International Application No. PCT/US2013/063513, dated Jan. 8, 2014, 21 pages.

Shapira et al., "Bolus Guide: A Novel Insulin Bolus Dosing Decision Support Tool Based on Selection of Carbohydrate Ranges," J Diabetes Sci Tech, 4(4): 893-902, Jul. 1, 2010.

Supplementary European Search Report in Application No. 13847858, dated May 31, 2016, 4 pages.

* cited by examiner

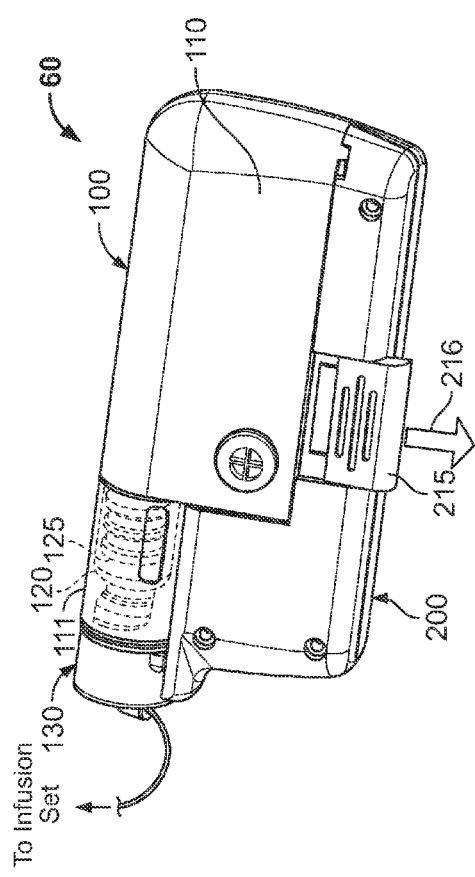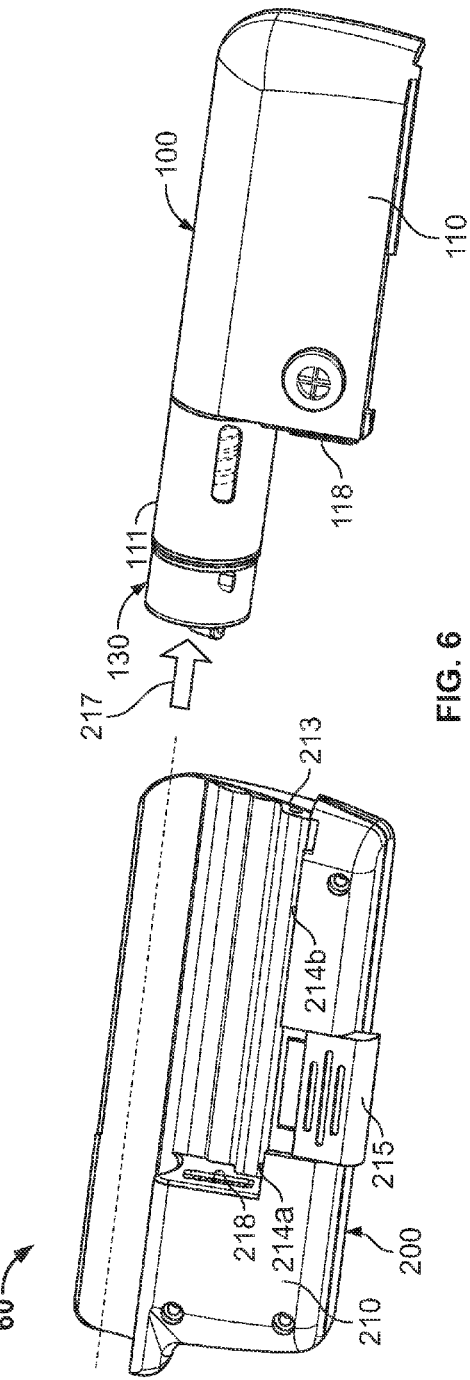

INFUSION PUMP SYSTEM AND METHODS

TECHNICAL FIELD

This disclosure relates to portable infusion pump systems to deliver fluids, such as insulin infusion pump systems or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood glucose levels.

Some embodiments of a medical infusion pump system can include a continuous glucose monitoring device for providing feedback data (e.g., blood glucose levels) to the infusion pump. The infusion pump, in turn, can process the data using its controller, which may take or suggest actions in response to the data. For example, the infusion pump's controller can provide an alarm if the blood glucose level is above or below a generally safe range.

In some embodiments, an insulin pump's controller may also provide an alarm if the controller predicts the patient's future blood glucose level will go above or below a threshold level. But, the ability of a pump's control algorithms to make an accurate prediction of the patient's future blood glucose level can be adversely affected by certain factors. For example, in some circumstances, the dosage of medicine delivered by the infusion pump acts within the patient's body over a long period of time. Such conditions, for example, may cause a patient to have an amount of non-activated insulin in his or her system even hours after the insulin dosage was dispensed from the infusion pump device. If this non-activated insulin is not taken into account by the pump's controller when predicting the patient's future blood glucose levels, the accuracy of the prediction will be adversely affected. Similarly, it may take hours for food that was consumed by a patient to impart its full effect on the patient's blood glucose levels. In some circumstances, this factor can affect the accuracy of the blood glucose prediction.

SUMMARY

Some embodiments of an infusion pump system can provide an alarm (e.g., an alert, a safety alarm, or the like) and initiate or suggest other countermeasures in response to a predicted condition that exceeds an alarm limit parameter. In some circumstances, the infusion pump system can be configured to predict the user's future blood glucose level based at least in part upon the user's current blood glucose level, the trend of the user's blood glucose level, the user's insulin load (e.g., an estimated value of previously dispensed insulin that has not yet acted in the user's body), and optionally, the user's food-on-board (e.g., an estimate of the carbohydrate value (or other food value) consume by the user that has not yet acted on the user, for example, metabolized for conversion into glucose).

Accordingly, if the predicted blood glucose level is outside the defined limit parameters, some embodiments of the infusion pump system may provide an alert that, for example, prompts the user to approve one or more countermeasures for purposes of preventing the user's blood glucoses level from actually reaching the threshold level in the future. Such a predictive feature can be valuable to a user when the infusion pump is operated in conjunction with a blood glucose monitoring device. Methods to provide the user with a greater scope of information and greater control regarding their blood glucose level are provided herein. Moreover, the infusion pump system can be configured to provide an indication to a user that a blood glucose level in the future (e.g., a predicted blood glucose level) may reach an upper or lower threshold level, and thus the infusion pump system can suggest to the user to "consume carbohydrates" or "reduce insulin dose" (e.g., if the predicted blood glucose level is below a lower threshold limit) or suggest to the user to "increase insulin dosage" or "avoid consuming carbohydrates" (e.g., if the predicted glucose level is above an upper threshold limit). Such a result can be used to reduce the likelihood of the user's blood glucose level reaching an alarm limit, thereby more consistently maintaining the user's blood glucose level within a desired range over an extended period of time.

Particular embodiments described herein include a medical infusion pump system. The system may include a portable pump housing that receives insulin for dispensation to a user, and the pump housing may at least partially containing a pump drive system to dispense the insulin through a flow path to the user. The system may also include a controller that communicates with the pump drive system to dispense the insulin from the portable pump housing. Optionally, the controller can be embodied as a removable controller device that is configured to releasably attach to the pump housing. The system may further include a monitoring device that communicates glucose information to the controller, and the glucose information may be indicative of a blood glucose level of the user. The controller can be configured to predict a future blood glucose level of the user based at least in part upon a recent blood glucose level, a trend of blood glucose levels over time, and an insulin load of the user. The controller may be configured to output an alarm in response to the predicted future blood glucose level being less than a lower threshold value or greater than a higher threshold value.

Some embodiments described herein include a controller for an insulin infusion pump system. The controller may include a processor, and one or more computer-readable memory devices to store the glucose information received from the monitoring device and time values associated with the glucose information. The one or more computer-readable memory devices may also store computer-readable instructions for a blood glucose prediction process that, when executed by the processor, cause the controller to perform a number of operations. The computer-readable instructions for the blood glucose prediction process may cause the controller to calculate a predicted future blood glucose level of the user based at least in part upon a recent blood glucose level of a user, a trend of blood glucose levels over time, and an insulin load of the user. The computer-readable instructions for the blood glucose prediction process may cause the controller to output an alarm in response to the predicted future blood glucose level being less than a lower threshold value. The computer-readable instructions for the blood glucose prediction process may cause the controller to operate in a low glucose recovery mode in response to user input that accepts activation of the low glucose recovery mode. Optionally, the controller can be embodied as a removable controller device that is configured to releasably attach to a pump housing for dispensing insulin.

Other embodiments described herein include a method of operating an insulin infusion pump system. The method may include receiving, at a controller of an insulin infusion pump system, glucose information indicative of a glucose level of a user. The method may also include determining an insulin load value indicative of an estimated value of previously dispensed insulin that has not yet acted in the user. The method may further include calculating, at the controller of the insulin infusion pump system, a predicted future blood glucose level of the user based at least in part upon a recent glucose level of the user, a trend of blood glucose levels over time, and the insulin load of the user. The method may also include, in response to the predicted future blood glucose level being less than a lower threshold value or greater than a higher threshold value, outputting an alarm from the insulin infusion pump system. Optionally, the controller can be embodied as a removable controller device that is configured to releasably attach to a pump housing of the insulin infusion pump system.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5-6 are perspective views of a pump device being detached from a controller device of the system of FIG. 1, in accordance with some embodiments.

Like reference symbols in the various drawings indicate like elements.

DETAILED DESCRIPTION OF ILLUSTRATIVE EMBODIMENTS

Figure 1:
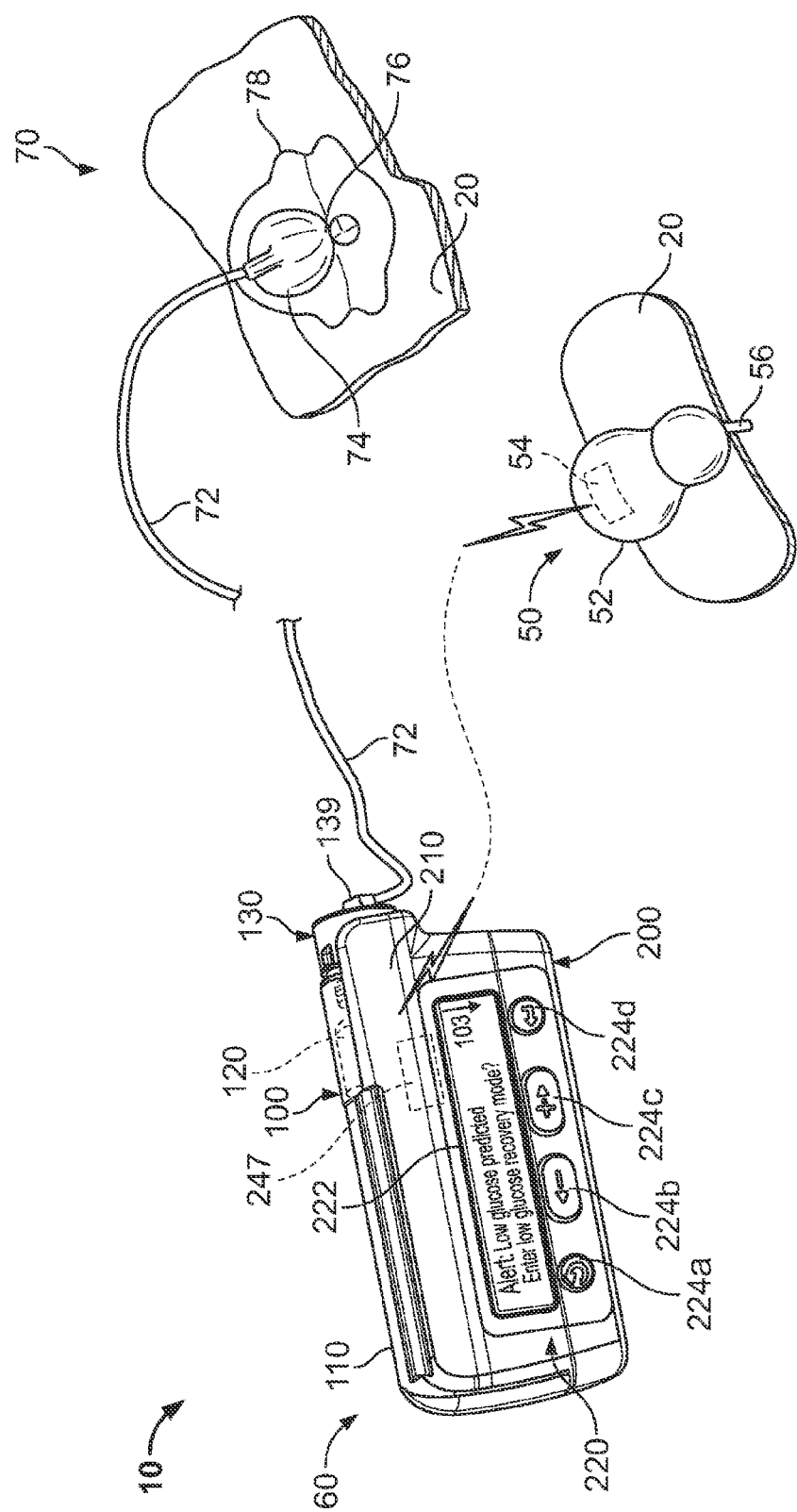
FIG. 1 is a perspective view of an infusion pump system, in accordance with some embodiments.

Referring to FIG. 1, an infusion pump system 10 can include a pump assembly 60 used to supply insulin or other medication to a user via, for example, an infusion set 70. In some embodiments, a glucose monitoring device 50 can be in communication with the infusion pump assembly 60 for the purpose of supplying data indicative of a user's blood glucose level to a controller device 200 included in the pump assembly 60. The infusion pump system 10 can utilize the data indicative of a user's blood glucose level to, for example, provide an alarm (e.g., an audible or textual safety alarm, an audible or textual alert notification, or another type of alarm) when the user's blood glucose level falls below a low glucose alarm limit or rises above a high glucose alarm limit. In some embodiments, as described further below in connection with FIGS. 11-14, the user's blood glucose data can be employed by the controller device 200 to predict the user's future blood glucose level. If the predicted blood glucose level is below a lower alarm limit, the controller device 200 can provide an alarm (e.g., audible, visual such as the display 222 of FIG. 1, or both) and prompt the user to approve particular countermeasures.

In some embodiments, the infusion pump system 10 can be configured to supply scheduled basal dosages of insulin (or other medication) along with user-selected bolus dosages. The basal rate can be selected to maintain a user's blood glucose level in a target range during normal activity when the user is not eating or otherwise consuming food items. The selected bolus deliveries may provide substantially larger amounts of insulin to limit the blood glucose level during certain circumstances, such as the consumption of carbohydrates and other food items (e.g., a "meal bolus") or to lower an elevated glucose level (e.g., a "correction bolus"). Due in part to pharmacokinetic effects (e.g., the time it takes for insulin to enter the blood stream from the subcutaneous point of delivery) and pharmacodynamic effects (e.g., the time it takes for a concentration of insulin in the blood to have the physiological effect of lower blood glucose level), basal and bolus insulin dispensed into the user's system may not act instantaneously, but instead may act over a period of time to control the user's blood glucose level. As such, the user's body may include some amount of insulin that has not yet acted even while the infusion pump assembly 60 is activated to deliver additional dosages (basal, bolus, or a combination thereof). In these circumstances, the infusion pump assembly 60 can be used to determine a user's total insulin load (TIL), which can provide an estimate of the total amount of insulin which has been delivered but has not yet acted in the user's body. As described herein, the phrase "total insulin load" can include an estimate of previously dispensed insulin, such as the sum of recent bolus and basal activity, and may preferably include an estimated value of previously dispensed insulin that has not yet acted in the user's body. Alternatively, the infusion pump assembly 60 can be used to determine a user's insulin-on-board (IOB), which is an estimate based upon only bolus dosages that have been delivered but have not yet acted in the user's body.

In some embodiments, the controller device 200 can determine a user's TIL information (e.g., a user's TIL value, TIL % value, or the like) in a manner that accounts for both the bolus deliveries and the basal deliveries (not merely bolus deliveries alone, as is typical with insulin-on-board estimations). As described in more detail below, this process for determining a user's TIL value can accurately reflect basal rate changes and bolus infusions. For example, in some embodiments, a user can have different basal rates depending on the time of day (e.g., a higher basal rate during some parts of the day, a lower basal rate during the night, etc.) In further embodiments, the TIL information can be determined by the controller device 200 in a manner that also accounts for the user's previously consumed food (along with the previous basal and bolus deliveries). As described in more detail below, such a process for determining the TIL information can quantify both the previously dispensed insulin that has not yet acted on the user and the previously consumed food that has not yet been metabolized.

In some embodiments, data related to a user's insulin load, such as TIL values (or IOB estimates) and the times at which they were calculated, can be stored in one or more memory devices (described below) of the controller device 200. As described in more detail below in connection with FIGS. 11-14, this data can be advantageously used, for example, by the controller device 200 in a process to more accurately predict future blood glucose levels. For instance, generally, if a user's insulin load (TIL or IOB) is higher than normal, the chances of the user's blood glucose level falling is more likely. In these circumstances, the controller device 200 can employ not only the most recently measured blood glucose level and the more recent trend data of the user's blood glucose levels, but the controller device 200 can also account for the user's insulin load (TIL or IOB) so as to more accurately assess whether the user's future blood glucose level will fall below a lower alarm limit. In response to such a determination by a predictive blood glucose algorithm executed by the controller device 200, the controller device 200 may provide enhanced user safety by providing an alarm which can alert the user to a potentially dangerous upcoming decrease in blood glucose level sooner than if the low blood glucose level was not predicted (or was predicted based merely upon the trend data of previous glucose level measurements).

Optionally, in some embodiments, the user's blood glucose information (including a current blood glucose level and a recent trend of blood glucose levels) and the TIL or IOB values can be augmented with a food-on-board estimation. Again, as described below in connection with FIGS. 11-14, such factors can be input to the predictive algorithm executed by the controller device 200 and used to calculate an estimated future blood glucose level. The controller device 200 can provide alarms (such as safety alarms, alert notifications, or the like) indicating that a predicted "high" or "low" blood glucose level is likely to occur. Such alarms can benefit the user in that this information can be used by the controller device 200 to prompt corrective action (e.g., prompting the user to eat, prompting the user for input in order to suggest a bolus dosage, or the like) before the user's blood glucose level has risen or fallen out of a normal range.

Still referring to FIG. 1, the glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to the controller device 200 of the pump assembly 60.

In some embodiments, the monitoring device 50 may include a circuit that permits sensor signals (e.g., data from the sensor shaft 56) to be communicated to the communication device 54. The communication device 54 can transfer the collected data to the infusion pump assembly 60 (e.g., by wireless communication to a communication device 247 arranged in the pump assembly 60). In some embodiments, the monitoring device 50 can employ other methods of obtaining information indicative of a user's blood characteristics and transferring that information to the infusion pump assembly 60. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some embodiments, the monitoring device 50 can be in communication with the pump assembly 60 via a wired connection. In other embodiments of the pump system 10, test strips (e.g., blood test strips) containing a sample of the user's blood can be inserted into a strip reader portion of the pump assembly 60 to be tested for characteristics of the user's blood. Alternatively, the test strips (e.g., glucose test strips) containing a sample of the user's blood can be inserted into a glucose meter device (not shown in FIG. 1), which then analyzes the characteristics of the user's blood and communicates the information (via a wired or wireless connection) to the pump assembly 60. In still other embodiments, characteristics of the user's blood glucose information can be entered directly into the pump system 10 via a user interface on the controller device 200.

Figure 2:
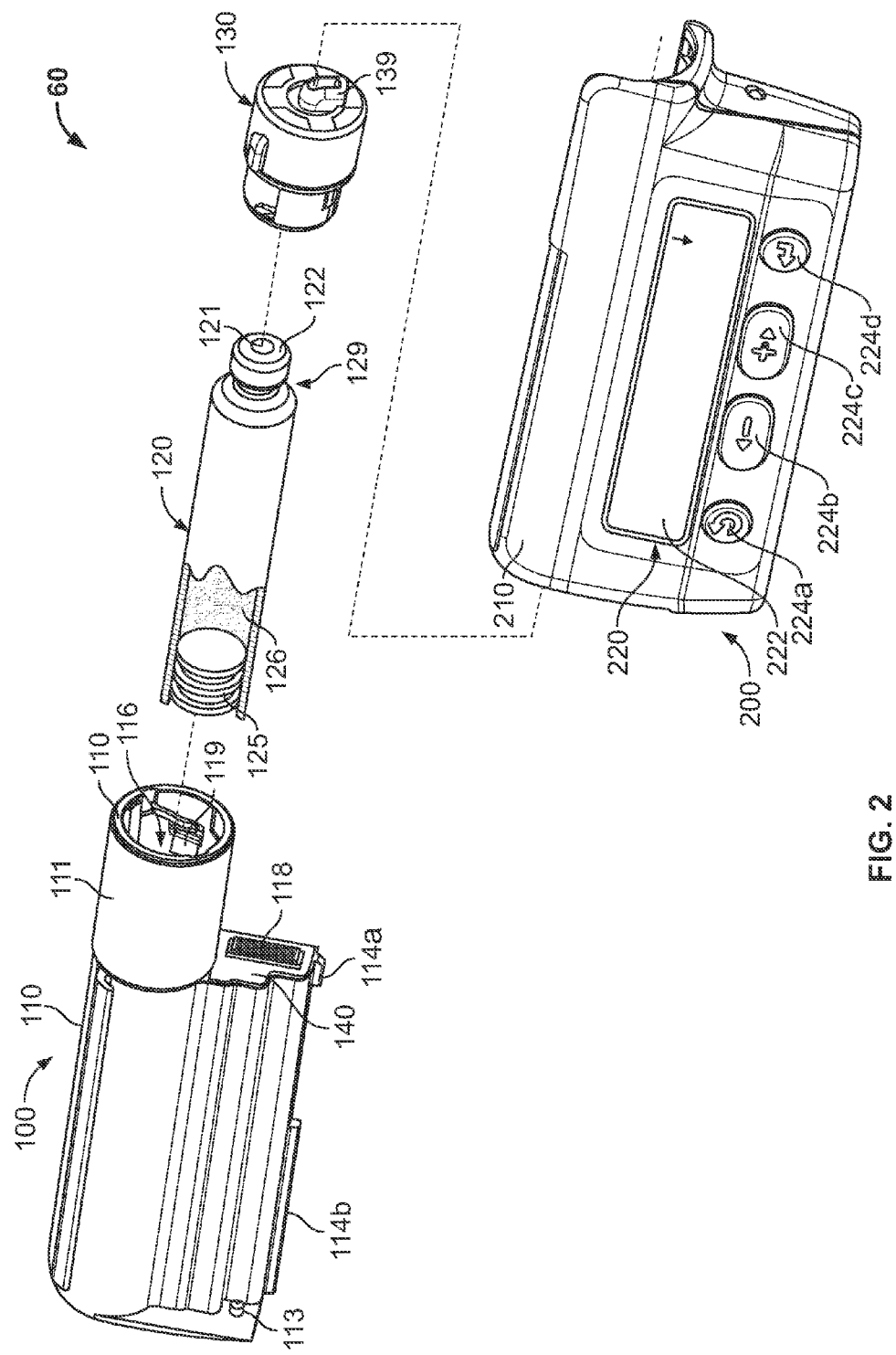
FIG. 2 is a perspective exploded view of an infusion pump assembly of the system of FIG. 1.

Referring now to FIGS. 1-2, the infusion pump assembly 60 can include a pump device 100 and the controller device 200 that communicates with the pump device 100. The pump device 100 includes a housing structure 110 that defines a cavity 116 in which a medicine cartridge 120 can be received. The pump device 100 also includes a cap device 130 to retain the medicine cartridge 120 in the cavity 116 of the housing structure 110. The pump device 100 includes a drive system (described in more detail below in connection with FIG. 10) that advances a plunger 125 in the medicine cartridge 120 so as to dispense fluid therefrom. In some embodiments, the dispensed fluid exits the medicine cartridge 120, passes through a flexible tube 72 of the infusion set 70 to a cannula housing 74. The dispensed fluid can enter through the skin via a cannula 76 attached to the underside of the cannula housing 74.

In some embodiments, the controller device 200 communicates with the pump device 100 to control the operation of the pump drive system. When the controller device 200, the pump device 100 (including the cap device 130 in this embodiment), and the medicine cartridge 120 are assembled together, the user may conveniently wear the infusion pump assembly 60 on the user's skin under clothing or in the user's pocket while receiving the fluid dispensed from the pump device 100 (refer, for example, to FIGS. 3-4). Thus, in some embodiments, the pump assembly can operate as a portable unit that provides reliable delivery of insulin or another medication in a discrete manner.

As described in more detail below, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the medicine cartridge 120 therein is exhausted. Thereafter, the user can removably attach a new pump device 100 to the reusable controller device 200 for the dispensation of fluid from a new medicine cartridge 120. Accordingly, the user is permitted to reuse the controller device 200 (which may include complex or valuable electronics) while disposing of the relatively low-cost pump device 100 after each use. Such a pump assembly 60 can provide enhanced user safety as a new pump device 100 (and drive system therein) is employed with each new medicine cartridge 120.

Briefly, in use, the pump device 100 can be configured to removably attach to the controller device 200 in a manner that provides a secure fitting, an overall compact size, and a reliable electrical connection. The compact size permits the infusion pump assembly 60 to be discrete and portable. As described in more detail below, the controller device 200 of the infusion pump system can be used to provide glucose alarms indicative of high and low blood glucose levels (when compared to predetermined high and low blood glucose alarm levels, respectively) and to predict high and low blood glucose levels based on insulin load information (e.g., TIL, IOB, TIL % value, and the like), blood glucose data, and, optionally, food-on-board information.

It should be understood that, in alternative embodiments, the pump device 100 and the controller device 200 can be configured as a single unit in which the control components and the pump drive system are arranged in a single housing. In these alternative embodiments, the pump assembly (including the controller device and the pump device) may have a different size and shape and may operate as a reusable unit that can communicate with a number of monitoring devices 50 over a period of time.

Referring again to FIGS. 1-2, in some embodiments, the pump system 10 is a medical infusion pump system that is configured to controllably dispense a medicine from the cartridge 120. As such, the medicine cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the medicine cartridge 120 include: medicines to treat primary immune deficiency (e.g., Vivaglobin® by CSL Behring of King of Prussia, Pa.), pain relief drugs, hormone therapy, blood pressure treatments, anti-emetics, osteoporosis treatments, or other injectable medicines. The medicine dispensed from the cartridge 120 into the user's system may act over a period of time in the user's body. As such, the user's body may include some amount of medicine that has not yet acted even while the infusion pump assembly 60 is activated to deliver additional dosages of the medicine (basal, bolus, or both). The infusion pump assembly 60 can be used to determine a user's total medicine load that provides an accurate indication of the medicine which has not yet acted in the user's body. The total medicine load can be determined by the controller device 200 in a manner that accounts for both the bolus deliveries and the basal deliveries of the medicine (similar to the process for determining the total insulin load as described below). It should be understood from the description herein that the medicine cartridge 120 may have a configuration other than that depicted in FIG. 2. For example, the medicine cartridge may have a different outer shape or a different reservoir volume. In another example, the medicine cartridge may comprise a reservoir that is integral with the pump housing structure 110 (e.g., the medicine cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 2, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 2) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100. Alternative embodiments can include other features and/or configurations to hinder the removal of the medicine cartridge 120.

Embodiments of the pump device 100 that hinder the removal of the medicine cartridge 120 may facilitate the "one-time-use" feature of the pump device 100. Because the retainer wings 119 can interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-2, the cap device 130 can be joined with the pump device 100 after the medicine cartridge is inserted in the cavity 116. It should be understood that the cap device 130 may supplement or replace the previously described retainer wings 119 by locking into position after joining with the pump housing 110, thereby hindering removal of the medicine cartridge 120 in the pump housing 110. As shown in FIGS. 1-2, the cap device 130 may include an output port 139 that connects with the tubing 72 for dispensation of the medicine to the user. In some embodiments, the output port 139 may have an angled orientation such that a portion of the tubing extends transversely to the central axis of the cartridge 120 and cap device 130. The output port 139 can be configured to mate with tubing 72 of the infusion set 70 (FIG. 1).

In some embodiments, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (described in connection with FIG. 10) of the pump device 100. As described in more detail below, the pump device 100 includes a drive system that causes controlled dispensation of the medicine or other fluid from the cartridge 120. In some embodiments, the drive system incrementally advances a piston rod longitudinally into the cartridge 120 so that the fluid is forced out of an output end 122. The septum 121 at the output end 122 of the medicine cartridge 120 can be pierced to permit fluid outflow when the cap device 130 is connected to the pump housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

The controller device 200 may be configured to removably attach to the pump device 100, for example, in a side-by-side arrangement. The compact size permits the infusion pump assembly 60 to be discrete and portable when the pump device 100 is attached with the controller device 200 (as shown in FIG. 1). In this embodiment, the controller device 200 includes a controller housing structure 210 having a number of features that are configured to mate with complementary features of the pump housing structure 110 so as to form a releasable mechanical connection (described below in more detail in connection with FIGS. 5-7). Such mating features of the pump housing structure 110 and the controller housing structure 210 can provide a secure connection when the controller device 200 is attached to the pump device 100.

As shown in FIG. 2, the pump device 100 may include an electrical connector 118 (e.g., having conductive pads, pins, or the like) that are exposed to the controller device 200 and that mate with a complementary electrical connector (refer to connector 218 in FIG. 6) on the adjacent face of the controller device 200. The electrical connectors 118 and 218 provide the electrical communication between the control circuitry (refer, for example, to FIG. 9) housed in the controller device 200 and at least a portion of the drive system or other components of the pump device 100. In some exemplary embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump assembly 60 may include a gasket 140 that provides a seal which is resistant to migration of external contaminants when the pump device 100 is attached to the controller device 200. Thus, in some embodiments, the pump device 100 and the controller device 200 can be assembled into a water resistant configuration that protects the electrical interconnection from water migration (e.g., if the user encounters water while carrying the pump assembly 60).

Referring again to FIGS. 1-2, the controller device 200 includes the user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed. For example, the display 222 may be used to communicate a number of status indicators, alarms, settings, and/or menu options for the infusion pump system 10. In some embodiments, the display 222 can indicate an alarm indicative of a high or low blood glucose level, high or low insulin load, the user's current IOB or TIL information, the user's blood glucose level, an indication that the user's blood glucose level is rising or falling, an indication that a blood glucose alarm level was modified, and the like. In the example depicted in FIG. 1, the display 222 indicates that an alert in which the controller device 200 has predicted that the user is likely to experience a low blood glucose level in the near future. In this embodiment, the display 222 also prompts the user to indicate whether he or she wants the pump device 100 to enter into a low glucose recovery mode so as to reduce the likelihood that the low blood glucose level (as predicted above) will actually occur, thereby helping the user to maintain blood glucose levels within the normal range.

In some embodiments, the user may press one or more of the buttons 224a, 224b, 224c, and 224d to shuffle through a number of menus or program screens that show particular status indicators, settings, and/or data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

The display 222 of the user interface 220 may be configured to display alarm information when no buttons 224a, 224b, 224c, and 224d have been pressed. For example, as shown in FIG. 1, the active area of the display 222 can display an alert indicating that the controller device 200 has predicted that the user will experience a low glucose level based at least in part upon the user's most recently measured blood glucose level, the trend of the user's blood glucose level over a recent period of time, the user's insulin load (e.g., TIL or IOB), and optionally, the user's food-on-board. The display 222 can also display the user's most recently measured blood glucose level (103 mg/dl in this example) and an indication of whether the user's blood glucose level is rising or falling (the downward facing arrow indicates a falling glucose level in this example). This information can be displayed until one of the buttons 224a, 224b, 224c, and 224d has been actuated. This, or other, information can also be displayed for a period of time after no button 224a, 224b, 224c, and 224d has been actuated (e.g., five seconds, 10 seconds, 30 seconds, 1 minute, 5 minutes, or the like).

Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 222 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the display 222 of the controller device 200. Such monitoring capabilities may provide comfort to a user who may have urgent questions about the current operation of the pump device 100 (e.g., the user may be unable to receive immediate answers if wearing an infusion pump device having no user interface attached thereto). Moreover, the TIL information can be displayed contemporaneously with the detected blood glucose value, so the user is provided with the opportunity to make informed decisions regarding the current and future status of his or her blood glucose level.

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200 without the requirement of locating and operating a separate monitoring module.

In other embodiments, the user interface 200 is not limited to the display and buttons depicted in FIGS. 1-2. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Figure 3:
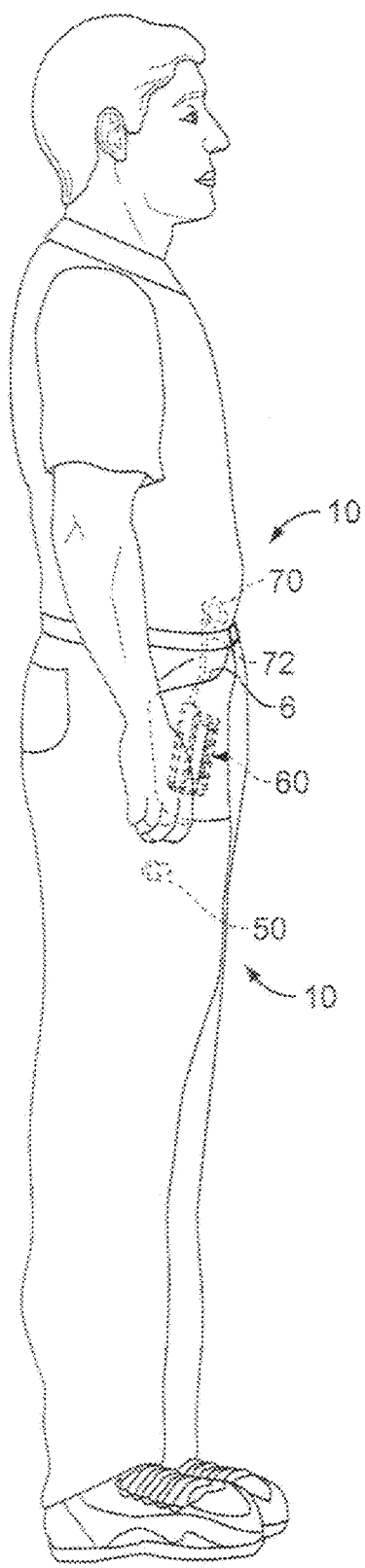
FIG. 3 is a perspective view of the infusion pump system of FIG. 1 in which the pump assembly is worn on clothing of a user, in accordance with particular embodiments.
Figure 4:
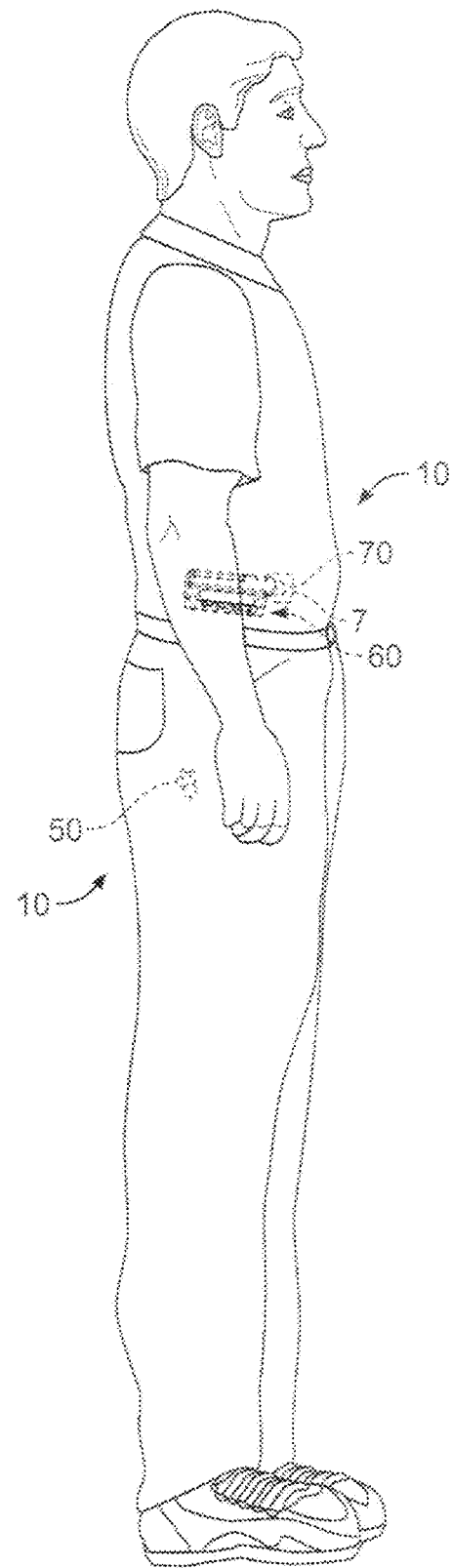
FIG. 4 is a perspective view of an infusion pump system of FIG. 1 in which the pump assembly is worn on skin of a user, in accordance with other embodiments.

Referring to FIGS. 3-4, the infusion pump system 10 may be configured to be portable and can be wearable and concealable. For example, a user can conveniently wear the infusion pump assembly 60 on the user's skin (e.g., skin adhesive) underneath the user's clothing or carry the pump assembly 60 in the user's pocket (or other portable location) while receiving the medicine dispensed from the pump device 100. The pump device 100 may be arranged in a compact manner so that the pump device 100 has a reduced length. For example, in the circumstances in which the medicine cartridge 120 has a length of about 7 cm or less, about 6 cm to about 7 cm, and about 6.4 cm in one embodiment, the overall length of the pump housing structure 110 (which contains medicine cartridge and the drive system) can be about 10 cm or less, about 7 cm to about 9 cm, and about 8.3 cm in one embodiment. In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump assembly 60 (including the removable controller device 200 attached to the pump device 100 having the cap 130) may have an overall length of about 11 cm or less, about 7 cm to about 10 cm, and about 9.6 cm in one embodiment; an overall height of about 6 cm or less, about 2 cm to about 5 cm, and about 4.3 cm in one embodiment; and an overall thickness of about 20 mm or less, about 8 mm to about 20 mm, and about 18.3 mm in one embodiment.

The pump system 10 is shown in FIGS. 3-4 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with the infusion set 70. In general, the infusion set 70 is tubing system that connects the infusion pump system 10 to the tissue or vasculature of the user (e.g., to deliver medicine into the user's subcutaneous tissue or vasculature). The infusion set 70 may include the flexible tube 72 that extends from the pump device 100 to the subcutaneous cannula 76 retained by a skin adhesive patch 78 that secures the subcutaneous cannula 76 to the infusion site. The skin adhesive patch 78 can retain the infusion cannula 76 in fluid communication with the tissue or vasculature of the patient so that the medicine dispensed through the tube 72 passes through the cannula 76 and into the user's body. The cap device 130 may provide fluid communication between the output end 122 (FIG. 2) of the medicine cartridge 120 and the tube 72 of the infusion set 70. For example, the tube 72 may be directly connected to the output port 139 (FIG. 2) of the cap device 130. In another example, the infusion set 70 may include a connector (e.g., a Luer connector or the like) attached to the tube 72, and the connector can then mate with the cap device 130 to provide the fluid communication to the tube 72. In these examples, the user can carry the portable infusion pump assembly 60 (e.g., in the user's pocket, connected to a belt clip, adhered to the user's skin, or the like) while the tube 72 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

Referring to FIG. 3, in some embodiments, the infusion pump assembly 60 is pocket-sized so that the pump device 100 and controller device 200 can be worn in the user's pocket 6 or in another portion of the user's clothing. For example, the pump device 100 and the controller device 200 can be attached together and form the assembly 60 that comfortably fits into a user's pocket 6. The user can carry the portable infusion pump assembly 60 and use the tube 72 of the infusion set 70 to direct the dispensed medicine to the desired infusion site. In some circumstances, the user may desire to wear the pump assembly 60 in a more discrete manner. Accordingly, the user may pass the tube 72 from the pocket 6, under the user's clothing, and to the infusion site where the adhesive patch 78 is positioned. As such, the pump system 10 can be used to deliver medicine to the tissues or vasculature of the user in a portable, concealable, and discrete manner. Furthermore, the monitoring device 50 can be worn on the user's skin while the pump assembly 60 is carried by the user (e.g., in a pocket). As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

Referring to FIG. 4, in other embodiments, the infusion pump assembly 60 may be configured to adhere to the user's skin 7 directly at the location in which the skin is penetrated for medicine infusion. For example, a rear surface of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 76 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220. Furthermore, the monitoring device 50 can be worn on the user's skin while the pump assembly 60 is worn on the user's skin in a different location from that where the monitoring device is worn. As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

In the embodiments depicted in FIGS. 3-4, the monitoring device 50 adheres to the user's skin 7 at the location in which the skin is penetrated by the sensor shaft 56 (to detect blood glucose levels). The sensor shaft 56 (refer to FIG. 1) penetrates the skin surface for the purpose of exposing the tip portion of the sensor shaft 56 to the tissue or the vasculature of the user. The sensor shaft 56 can detect information indicative of the user's blood glucose level and transfer this information to a circuit that is connected to the communications device 54 located within the monitoring device 50. The communication device 54 can be in wireless communication with the communication device 247 (described in connection with FIG. 9) included in the controller device 200 of the pump assembly 60.

Referring now to FIGS. 5-8, in some embodiments, the infusion pump assembly 60 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 (FIG. 2) is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new medicine cartridge 120.

Referring to FIGS. 5-6, the pump device 100 can be readily removed from the controller device 200 when the medicine cartridge 120 is exhausted. As previously described, the medicine cartridge 120 is arranged in the cavity 116 (FIG. 2) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length.

As shown in FIG. 5, the pump device 100 has been used to a point at which the medicine cartridge 120 is exhausted. The plunger 125 has been advanced, toward the left in FIG. 5, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 to determine if the medicine cartridge 120 is almost empty. When the user determines that a new medicine cartridge 120 should be employed, the pump device 100 can be readily separated from the controller device 200 by actuating a release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 5) away from the pump device 100 (e.g., by applying a force with the user's finger).

As shown in FIG. 6, when the release member 215 is actuated and moved to a position away from the pump device 100, a segmented guide rail 114a-b is free to slide longitudinally in a guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 2) may be withdrawn from the mating depression 213 (FIG. 6), and the electrical connector 118 can be separated from the mating connector 218. In these circumstances, the pump device 100 is physically and electrically disconnected from the controller device 200 while the pump device retains the exhausted medicine cartridge 120. It should be understood that, in other embodiments, other features or connector devices can be used to facilitate the side-by-side mounting arrangement. These other features or connector devices may include, for example, magnetic attachment devices, mating tongues and grooves, or the like.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., moved in the lateral direction 216 in the embodiment shown in FIG. 5). Accordingly, in some embodiments, the pump device 100 can automatically and sharply move a small distance (e.g., about 0.5 mm to about 5 mm) away from the controller device 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 7:
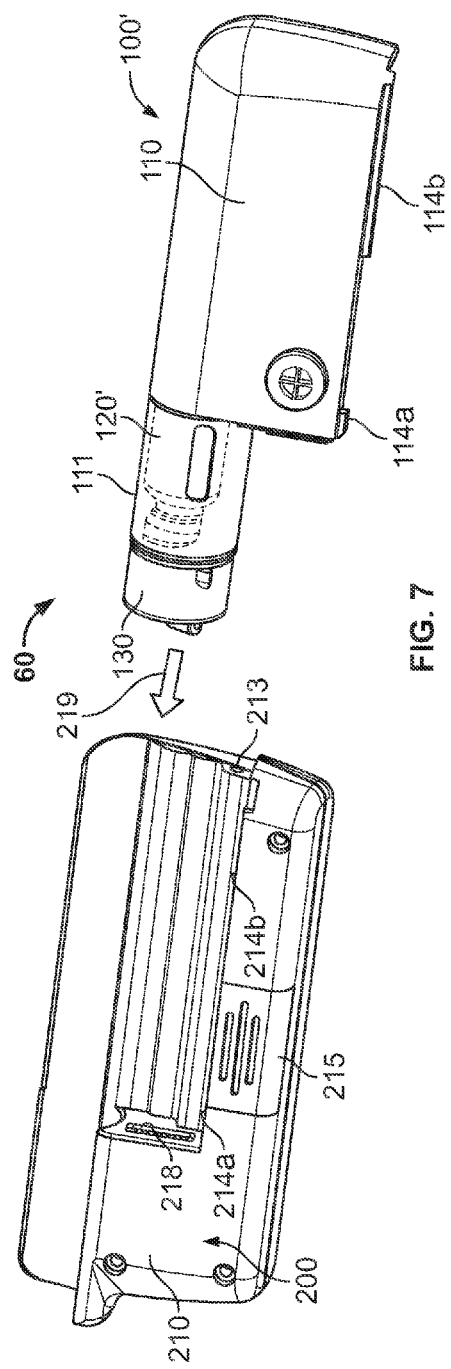
FIGS. 7-8 are perspective views of the pump device of FIGS. 5-6 being discarded and the controller device of FIGS. 5-6 being reused with a new pump device.
Figure 8:
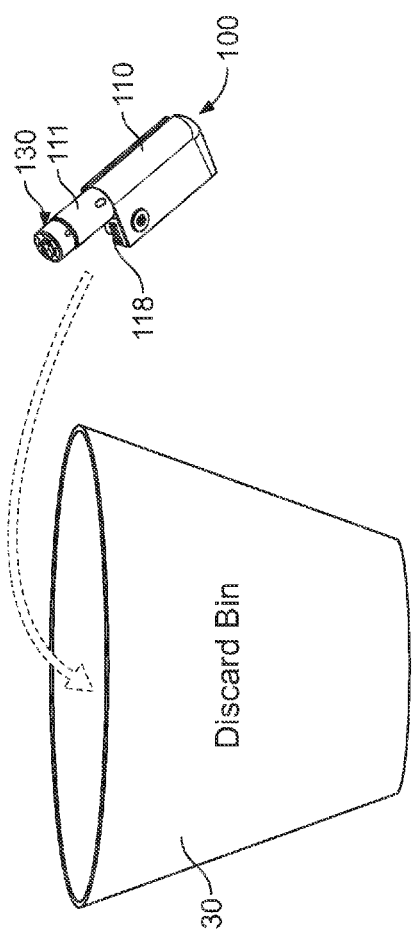

Referring to FIGS. 7-8, the same controller device 200 can be reused with a new pump device 100' having a new medicine cartridge 120' retained therein, and the previously used pump device 100 can be discarded with the exhausted medicine cartridge 120. The new pump device 100' (FIG. 7) can have a similar appearance, form factor, and operation as the previously used pump device 100 (FIGS. 5-6), and thus the new pump device 100' can be readily attached to the controller device 200 for controlled dispensation of medicine from the new medicine cartridge 120'. In some embodiments, the user may prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 2). Although the tubing 72 of the infusion set 70 is not shown in FIG. 7, it should be understood that the tubing 72 may be attached to the cap device 130 prior to the cap device 130 being joined with the housing 110. For example, a new infusion set 70 can be connected to the cap device 130 so that the tubing 72 can be primed (e.g., a selected function of the pump device 100 controlled by the controller device 200) before attaching the infusion set patch to the user's skin. As shown in FIG. 7, the new medicine cartridge 120' may be filled with medicine such that the plunger 125 is not viewable through the barrel 111. In some embodiments, the user can removably attach the pump device 100 to the controller device 200 by moving the pump device 100 in a longitudinal direction 219 toward the controller device 200 such that the segmented guide rail 114a-b engages and slides within the guide channel 214a-b. When the electrical connectors 118 and 218 mate with one another, the release member 215 can engage the segmented guide rails 114a-b to retain the pump device 100 with the controller device 200.

As shown in FIG. 8, the previously used pump device 100 that was separated from the controller device (as described in connection with FIGS. 5-6) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 30, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 70 (not shown in FIG. 8, refer to FIG. 1) that was used with the pump device 100 may be removed from the user and discarded into the bin 30 along with the pump device 100. Alternatively, the infusion set 70 can be disconnected from the previous pump device 100 and attached to the new pump device 100'. In these circumstances, the user may detach the infusion set cannula 76 and patch 78 from the skin so as to "re-prime" the tubing with medicine from the new pump device 100' to remove air pockets from the tubing. Thereafter, the infusion set cannula 76 and patch 78 can be again secured to the user's skin.

Figure 9:
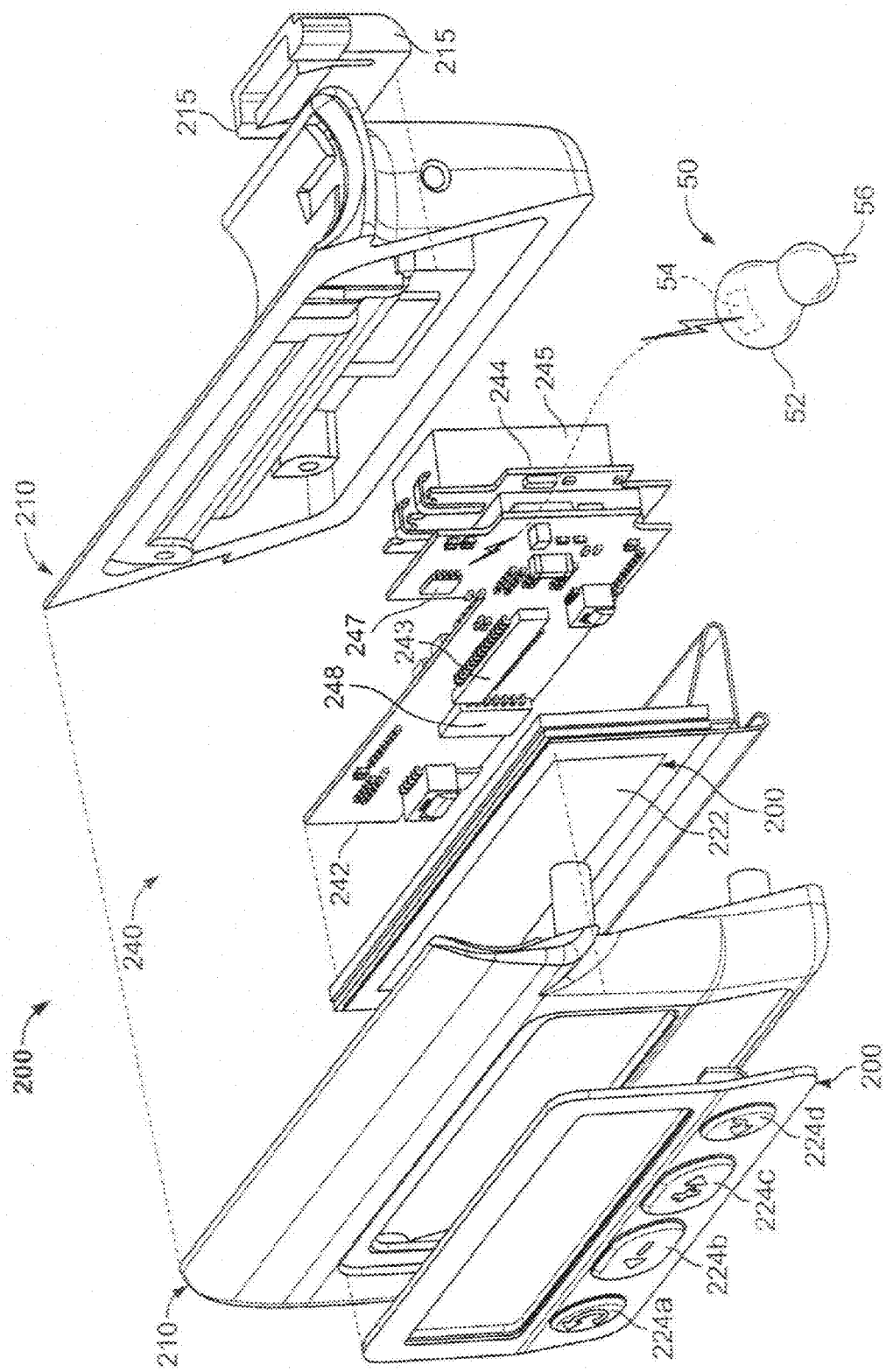
FIG. 9 is an exploded perspective view of a controller device for an infusion pump system, in accordance with some embodiments.

Referring now to FIG. 9, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices (e.g., memory chip 248). It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the one or more memory devices, such as the memory chip 248 on the processor board 242. The control circuitry 240 may include other components, such as sensors (e.g., occlusion sensors), that are electrically connected to the main processor board 242. Furthermore, the control circuitry 240 may include one or more dedicated memory devices that store executable software instructions for the processor 243. The one or more memory devices (e.g., the memory chip 248) can also store information related to a user's blood glucose level and total insulin load (described in more detail in association with FIGS. 11-16B) over a period of time.

As previously described, the controller device 200 can be electrically connected with the pump device 100 via mating connectors 118 and 218 so that the control circuitry 240 can communicate control signals to the pump device 100 and receive feedback signals from components housed in the pump device 100. In this embodiment, the electrical connector 118 (FIG. 2) on the pump device 100 is a z-axis connector, and the connector 218 (FIG. 6) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Still referring to FIG. 9, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of status indicators, settings, and/or menu options for the infusion pump system 10. In some embodiments, the control circuitry 240 may receive the input commands from the user's button selections and thereby cause the display device 222 to output a number of status indicators (e.g., if the pump system 10 is delivering insulin, if the user's blood glucose level is rising or falling, and the like), menus, and/or program screens that show particular settings and data (e.g., the user's blood glucose level, the user's insulin load, the user's TIL % value, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port, another data cable port, or a data cable connection via the electrical connection 218) that is accessible on an external portion of the controller housing 210. As such, a cable may be connected to the control circuitry 240 to upload data or program settings to the controller circuit or to download data from the control circuitry 240. For example, historical data of blood glucose level, blood glucose alarm limits (including notification alert limits and safety alarm limits), medicine delivery (including basal and bolus deliveries), and/or TIL information can be downloaded from the control circuitry 240 (via the cable connector) to a computer system of a physician or a user for purposes of analysis and program adjustments. Optionally, the data cable may also provide recharging power.

Figure 10:
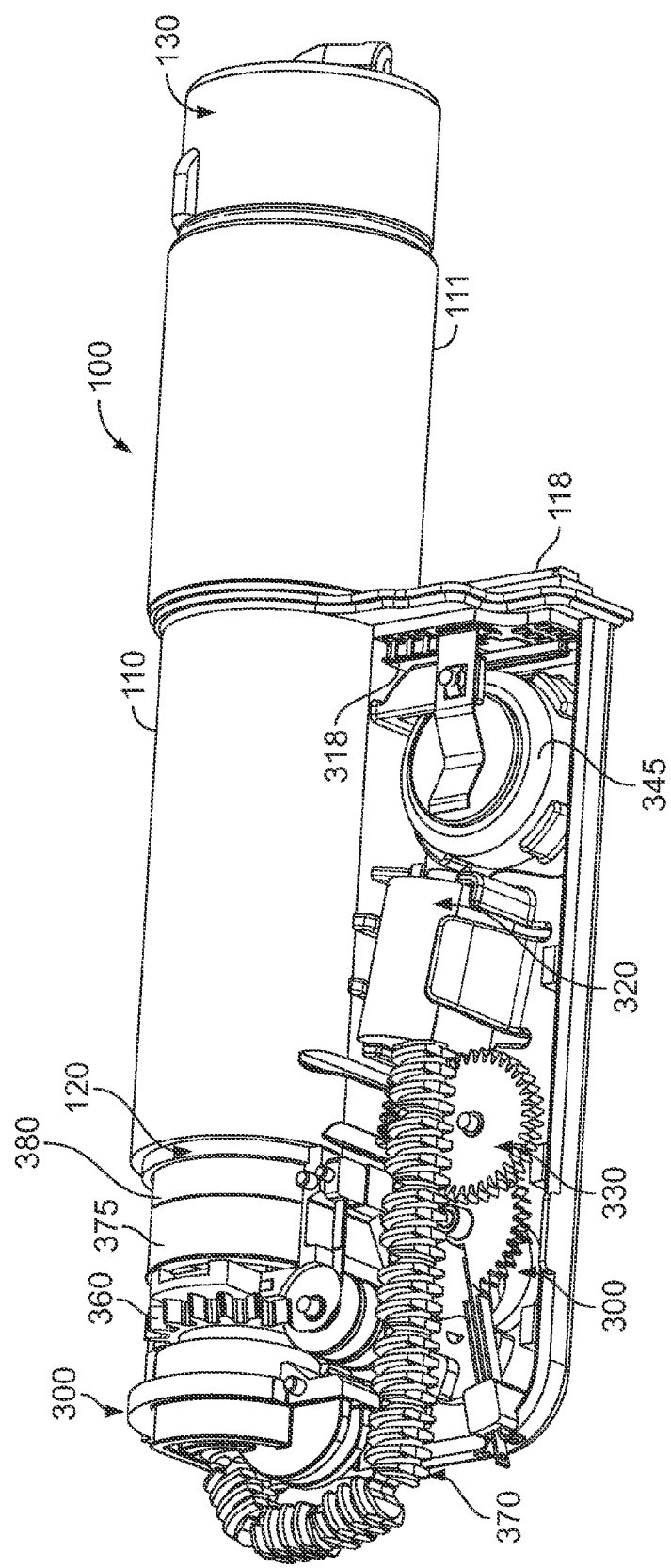
FIG. 10 is a perspective view of a portion of a pump device for an infusion pump system, in accordance with particular embodiments.

Referring to FIGS. 9-10, the control circuitry 240 of the controller device 200 may include a second power source 245 (FIG. 9) that can receive electrical energy from a first power source 345 (FIG. 10) housed in the pump device 100. In this embodiment, the second power source 245 is coupled to the power supply board 244 of the control circuitry 240. The hard-wired transmission of the electrical energy can occur through the previously described connectors 118 and 218. In such circumstances, the first power source 345 may include a high density battery that is capable of providing a relatively large amount of electrical energy for its package size, while the second power source 245 may include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, the first battery 345 may comprise a zinc-air cell battery. The zinc-air cell battery 345 may have a large volumetric energy density compared to some other battery types. Also, the zinc-air cell battery may have a long storage life, especially in those embodiments in which the battery is sealed (e.g., by a removable seal tab or the like) during storage and before activation.

The second battery 245 may include a high current-output device that is housed inside the controller housing 210. The second battery 245 can be charged over a period of time by the first battery 345 and then intermittently deliver bursts of high-current output to the drive system 300 over a brief moment of time. For example, the second battery 245 may comprise a lithium-polymer battery. The lithium-polymer battery 245 disposed in the controller device 200 may have an initial current output that is greater than the zinc-air cell battery 345 disposed in the pump device 100, but zinc-air cell battery 345 may have an energy density that is greater than the lithium-polymer battery 245. In addition, the lithium-polymer battery 245 is readily rechargeable, which permits the zinc-air battery 345 disposed in the pump device 100 to provide electrical energy to the lithium-polymer battery 245 for purposes of recharging. In alternative embodiments, it should be understood that the second power source 245 may comprise a capacitor device capable of being recharged over time and intermittently discharging a current burst to activate the drive system 300.

Accordingly, the infusion pump system 10 having two power sources 345 and 245—one arranged in the pump device 100 and another arranged in the reusable controller device 200—permits a user to continually operate the controller device 200 without having to recharge a battery via an outlet plug-in or other power cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Referring now to FIG. 10, the pump device 100 in this embodiment includes the drive system 300 that is controlled by the removable controller device 200 (see FIG. 2). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. Some embodiments of the drive system 300 may include a battery powered actuator (e.g., reversible motor 320 or the like) that actuates a gear system 330 to reset a ratchet mechanism (e.g., including a ratchet wheel and pawl), a spring device (not shown) that provides the driving force to incrementally advance the ratchet mechanism, and a drive wheel 360 that is rotated by the ratchet mechanism to advance the flexible piston rod 370 toward the medicine cartridge 120. Connected to piston rod 370 is a plunger engagement device 375 for moving the plunger 125 of the medicine cartridge 120.

Some embodiments of the drive system 300 can include a pressure sensor 380 disposed between the plunger engagement device 375 and the plunger 125 for determining the pressure within the fluid path (e.g., inside the medicine cartridge 120, the infusion set 70, and the like). For example, the fluid pressure in the medicine cartridge 120 can act upon the plunger 125, which in turn can act upon the pressure sensor 380 arranged on the dry side of the plunger 125. The pressure sensor 380 may comprise a pressure transducer that is electrically connected (via one or more wires) to a gateway circuit 318 so that the sensor signals can be communicated to the controller device 200 (e.g., via the electrical connectors 118 and 218). As such, data from the pressure sensor 380 can be received by the controller device 200 for use with, for example, an occlusion detection module to determine if an occlusion exists in the medicine flow path. Alternatively, the controller device 200 may include an optical sensor system (not shown in FIGS. 9-10) to detect occlusions in the fluid path. For example, a light emitter and light sensor may each be arranged on a sensor circuit in the controller device 200 (but aligned with the pump device 100) so that the light sensor can detect the amount of light emitted by the light emitter and subsequently reflected from a component adjacent the fluid path. The reflected light level detected may be used to determine the pressure within the fluid path.

Figure 11:
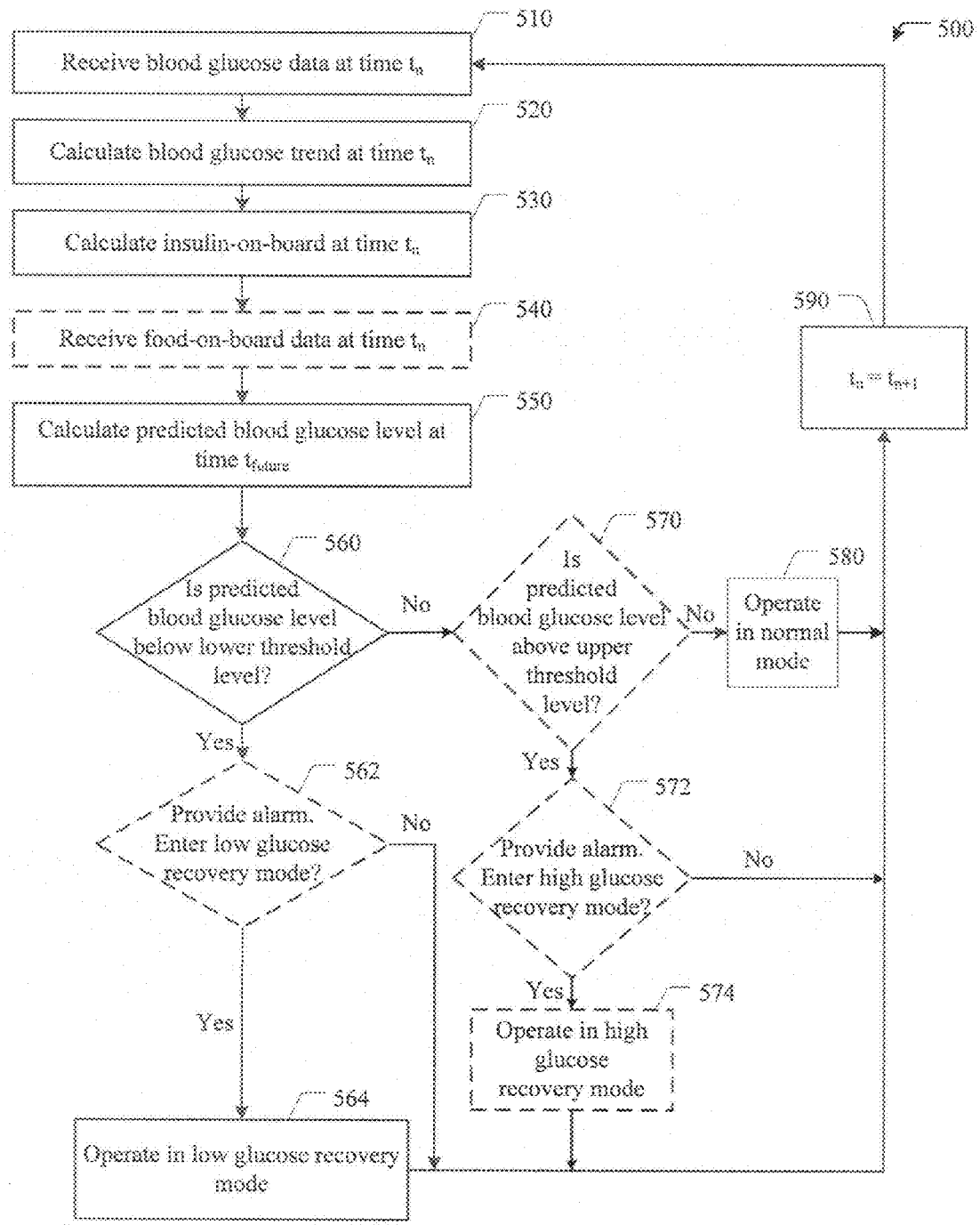
FIG. 11 is a flow diagram depicting an exemplary process used to determine a user's predicted blood glucose level, in accordance with some embodiments.

Referring now to FIG. 11 which illustrates how, in some embodiments, the controller device 200 of infusion pump system 10 can be used to predict a user's blood glucose level at a particular future point in time. In general, the flow diagram depicts a process 500 that can be executed by the pump controller device 200 that collects the necessary data to calculate a blood glucose prediction, performs calculations, determines whether to provide an alarm based on the predicted blood glucose level, prompts the user for input as to whether to take corrective action(s), and performs the corrective action(s) in accordance with the user's response. The sub-process of collecting the data and making the calculations can be repeated on a periodic basis, such as every 1 minute, every 2 minutes, every 5 minutes, or on any other appropriate time frequency basis.

At operation 510, the pump controller device 200 receives a user's blood glucose data at time $t_n$. The data is stored in the computer-readable memory of the controller device 200. The blood glucose data can be provided to the pump controller device 200 in a number of ways. For example, the infusion pump system 10 (refer, for example, to FIG. 1) can include a glucose monitoring device such as glucose monitoring device 50 of FIG. 1. In such a system, the glucose monitoring device 50 can be in communication with the pump assembly 60 via wireless communications or a wired connection. In other embodiments of the pump system 10, test strips (e.g., blood test strips) containing a sample of the user's blood can be inserted into a strip reader portion of the pump assembly 60 that can test for the blood glucose level of the user's blood. Alternatively, the test strips (e.g., glucose test strips) containing a sample of the user's blood can be inserted into a separate glucose meter device (not shown), which can then analyze the characteristics of the user's blood and communicate the information (via a wired or wireless connection) to the pump assembly 60. In still other embodiments, characteristics of the user's blood glucose information can be entered directly into the pump system 10 via a user interface on the controller device 200. Using such example techniques, the controller device 200 can receive the user's blood glucose reading at point in time $t_n$.

At operation 520, the pump controller device 200 can calculate the user's blood glucose trend information at $t_n$. For example, the glucose trend information can be determined using a curve-fit model that looks for blood glucose fluctuation patterns or trends can be applied to stored recent set of blood glucose measurements stored in the memory of the controller device 200 to thereby provide a rough indication of a user's blood glucose level at a time in the near future. Alternatively, the glucose trend information can be calculated in the monitoring device and then communicated to the controller device 200 for storage and use in this method. As described in more detail below, by using the blood glucose trend information and along with other factors (such as the user's TIL or IOB and, optionally, the food-on-board estimate), the accuracy of blood glucose predictions can be significantly improved and provide additional benefits to the user.

The blood glucose trend can be calculated, for example, based on a predictive statistical model applied to past blood glucose data points. In one such example, blood glucose data equations can be curve-fit and extrapolated using linear regression techniques to estimate the blood glucose trajectory. In another example, the straight-line slope of the recent blood glucose data points can be determined and the slope of the fitted-line can be extrapolated to provide a prediction.

At operation 530, the user's insulin load (e.g., an estimated amount of insulin already delivered to the user's body, such as the TIL or IOB) at time $t_n$ can be calculated. In the depicted embodiment, the process 500 employs the IOB estimate for the user's insulin load. IOB accounts for bolus insulin dosages (but not basal dosages) that have been delivered but have not yet acted in the user's body. In general, the user may select one or more bolus deliveries, for example, to offset the blood glucose effects caused by the intake of food (e.g., a "meal bolus" of insulin) or to correct for an undesirably high blood glucose level (e.g., a "correction bolus" of insulin). The bolus dosages can be dispensed in user-selected amounts based on calculations made by the controller device 200. For example, the controller device 200 can be informed of a high glucose level (e.g., by user input, data received from the glucose monitoring device 50, or the like) and can make a suggestion to the user to administer a bolus of insulin to correct for the high blood glucose reading (e.g., a "correction bolus"). In another example, the user can request that the controller device 200 calculate and suggest a bolus dosage based, at least in part, on a proposed meal that the user plans to consume (e.g., a "meal bolus"). As described in more detail below in connection with operation 550, some implementations of the process 500 may rely upon an IOB value that accounts for all bolus dosages (e.g., including both meal boluses and correction bolus) that have been delivered but have not yet acted in the user's body. In other implementations, the process 500 may rely upon an IOB value that accounts for only correction bolus dosages (e.g., exclude meal bolus dosages) that have been delivered but have not yet acted in the user's body (especially in circumstances where the user's FOB component is also excluded from the calculation).

The insulin dispensed into the user's system may act over a period of time to control the user's blood glucose level. As such, the user's body may include some amount of insulin that has not yet acted. The user's future blood glucose level is likely to decline as the insulin load takes effect over time. Because the IOB has a potential for causing a future drop in blood glucose, the process 500 can more accurately and more rapidly predict a low blood glucose event.

The IOB can be determined in a manner that accounts for the substantial delay between the time that insulin is delivered to the tissue of the subcutaneous region and the time that this insulin reaches the blood supply. For example, the delay between a subcutaneous delivery of a bolus dosage of insulin and the peak plasma insulin level achieved from this bolus can be one hour or more. Additionally, the bolus dosage may not enter the blood stream all at once. As such, the effect of the bolus can peak at about one to two hours and then decay in a predictable manner over as much as eight hours or more (described in more detail in connection with FIG. 12). Due to the time decay effects of insulin activity, the user could be susceptible to request a subsequent bolus dosage while some insulin from a previously delivered bolus dosage has not yet acted upon the user (a scenario sometimes referred to as "bolus stacking"). To reduce the likelihood of undesirable bolus stacking, and to improve the accuracy of a prediction of the user's future blood glucose level, the IOB information can be determined by the controller device 200 and subsequently used as a factor in a calculation of the user's predicted blood glucose level at a future time.

Figure 12:
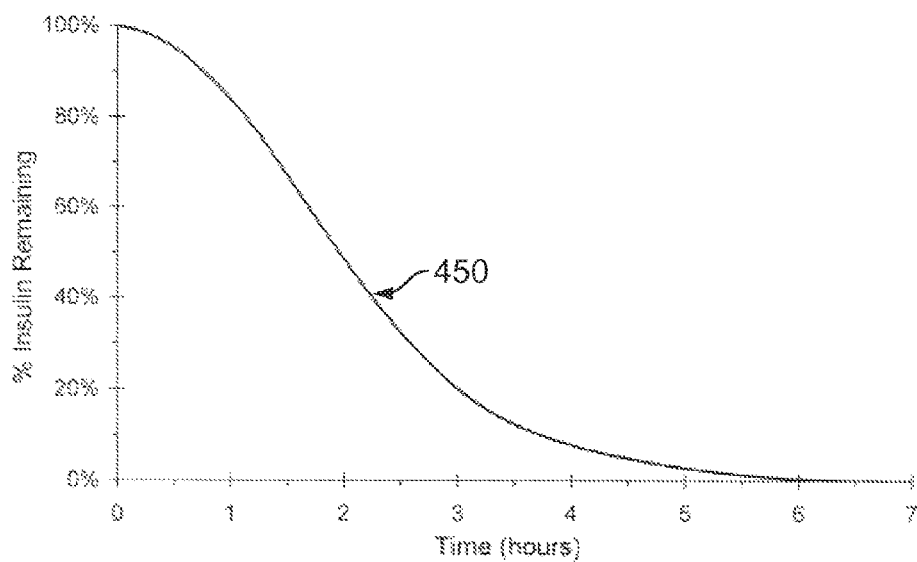
FIG. 12 is a diagram depicting an example of an insulin decay curve, which may be employed in the determination of the user's total insulin load (TIL) or insulin-on-board (IOB) in accordance with some embodiments.

In some embodiments, the controller device 200 can determine the IOB at time $t_n$ based on bolus dosages that have been delivered to the patient in the recent past. In some embodiments, for each bolus dosage dispensed within a predetermined period of time before $t_n$ (e.g., 6 hours, 7 hours, 7.5 hours, 8 hours, 10 hours, or the like), the controller device 200 can estimate the amount of bolus insulin that has not yet acted in the blood stream from time-decay models generated from pharmacodynamic data of the insulin. For example, a graph of an exemplary curve depicting the percent of insulin remaining versus time can be seen in FIG. 12. In particular, FIG. 12 illustrates an example of the insulin action curve generated from pharmacodynamic data for the insulin stored in the cartridge 120. Thus, in this embodiment, the IOB calculation represents the sum of all recent bolus insulin dosages wherein each bolus insulin dosage is discounted by the active insulin function (which may be modeled on pharmacodynamic data as shown, for example, in FIG. 12). In this manner, for example, the IOB can be calculated at operation 530.

Optionally, the process 500 may include operation 540 in which food-on-board data at a period in time $t_n$ is received or otherwise determined by the controller device 200. The rationale for including the food-on-board information in a predictive blood glucose algorithm is that it takes time for carbohydrates consumed by a person to be metabolized such that their full effects on the person's blood glucose level are realized. Therefore, yet-to-be-metabolized carbohydrates may have a direct impact on future blood glucose levels, and incorporating such information can improve the accuracy of the process 500 for predicting future blood glucose levels.

The controller device 200 can determine the food-on-board data component based on, for example, the total carbohydrates previously entered into the controller device 200 as being consumed by the user during a predetermined period of time before $t_n$ (e.g., 6 hours, 7 hours, 7.5 hours, 8 hours, 10 hours, or the like). The previous food component can be determined, for example, by estimating the amount of carbohydrates that have been consumed but not yet metabolized by the user's body so as to affect the blood glucose level. For each of the previous food items reported by the user, the controller device 200 can estimate the previously consumed food that has not yet been metabolized from a time-based model generated from a standard glycemic index. Alternatively, when the user enters information regarding food intake, the user can be prompted to identify the metabolization "speed" of the food item based on the glycemic index for that food. In these circumstances, the user may be prompted to input the amount of food (e.g., grams of Carbohydrate or another representative value) and then identify the glycemic index (via a numerical scale or from a list of two or more choices (e.g., "fast" metabolization and "slow" metabolization) to provide a more accurate time-based function for specific meals. When this yet-to-be-metabolized carbohydrate value is estimated, it can be treated as a "negative" insulin component in the predictive blood glucose calculation by multiplying the yet-to-be-metabolized carbohydrate value by a carbohydrate ratio (e.g., 1 unit of insulin per 15 grams of carbohydrates). In some embodiments, the calculated value for the food-on-board component can be displayed separately to the user (e.g., to provide the user with information regarding the effects of the previously consumed carbohydrates).

At operation 550, a predicted value for the user's future blood glucose level can be calculated by the controller device 200. In general, the calculation can incorporate the data components described above in regard to process 500, such as the recently measured blood glucose level (at $t_n$), the trend model calculated from the recent set of blood glucose measurements over a recent period of time, the IOB (at $t_n$), and optionally the food-on-board at ($t_n$). In addition, an insulin sensitivity factor (Si) can be included in the calculation. The insulin sensitivity factor represents the effect on a particular user's blood glucose level in response to receiving a unit of insulin.

In a first preferred embodiment, the predicted value for the user's future blood glucose level (PBG) can be calculated according to the following algorithm that is executed by the pump controller:

$$PBG=BG+R*T-IOB*Si+Si*FOB/C$$

where:
PBG is the predicted blood glucose level;
BG is the blood glucose level at $t_n$;
R is the rate of change of the trend of past blood glucose data points;
T is the time increment into the future that the calculated PBG pertains to;
IOB is the bolus insulin-on-board (JOB) at $t_n$ as described above;
Si is the insulin sensitivity factor (amount of blood glucose change per unit of insulin);
FOB is the food-on-board at $t_n$ estimate; and
C is the estimated carbohydrate ratio of the FOB (amount of carbohydrates per unit of insulin).

The following example is provided to illustrate the formula above. This example assumes the following data inputs:
BG (the blood glucose level at $t_n$)=120 mg/dL;
R (the rate of change of past BG data points)=−2 mg/dL/min;
T (the time increment into the future)=10 minutes;

IOB at $t_n$=3 units;
Si (the user's insulin sensitivity factor)=20 mg/dL/unit;
FOB (the food-on-board at $t_n$)=40 g; and
C (the carbohydrate ratio of the FOB)=20 g/unit.
Incorporating the above values in the aforementioned algorithm for calculating a predicted blood glucose level (PBG) provides a value of:

$$PBG=120 \text{ mg/dL}+(-2 \text{ mg/dL/min})*10 \text{ min}-3 \text{ units}*20 \text{ mg/dL/unit}+20 \text{ mg/dL/unit}*(40 \text{ g})/(20 \text{ g/unit})=80 \text{ mg/dL}.$$

Hence, the algorithm above has predicted that the user's blood glucose level 10 minutes in the future from $t_n$ will be 80 mg/dL, in comparison to the current level of 120 mg/dL (at $t_n$). In contrast, if the IOB and the FOB were not included in the calculation, the PBG would have been 100 mg/dL. This example illustrates that including IOB estimate and, optionally, the food-on-board estimate in the predictive calculation of blood glucose can likely improve the accuracy of the prediction.

The value for T (the time increment into the future of the predictive calculation) can be selected based on a balance of practical factors including: the user's ability to respond in a timely manner, the time needed for countermeasures to take effect, and the user's desired level of control. In this embodiment, the value for T is a predetermined parameter set by the supplier of the pump controller device 200. In alternative embodiments, the value for T can be an adjustable parameter that is selected by the user's clinician or the user himself or herself. In some embodiments, the value for T can be selected from a range of 5-60 minutes, selected from a range of 5-30 minutes, and (in this embodiment), selected to be 10 minutes in the example above.

As previously described, the value for the parameter Si can be different for different users, and as such a particular user may use his or her individualized value for the improved accuracy of the blood glucose prediction. The Si for a particular user can be input to the user's controller device 200 via the user interface 220, for example, by the user's clinician or the user himself or herself.

In a second preferred embodiment, the predicted value for the user's future blood glucose level (PBG) can be calculated according to the following algorithm that is executed by the pump controller:

$$PBG=BG+R*T-TIL*Si+Si*FOB/C,$$

where:
PBG is the predicted blood glucose level;
BG is the blood glucose level at $t_n$;
R is the rate of change of the trend of past blood glucose data points;
T is the time increment into the future that the calculated PBG pertains to;
TIL is the Total Insulin Load at $t_n$ as described above;
Si is the insulin sensitivity factor;
FOB is the food-on-board at $t_n$ estimate; and
C is the estimated carbohydrate ratio of the FOB.
This formula is different from the first preferred embodiment in that it employs the TIL estimate instead of the IOB estimate. In other words, the not-yet-acted insulin that was delivered to the user as any of bolus dosages and basal dosages is included in this algorithm (not merely insulin from the bolus dosages). In some embodiments, the calculation of TIL can be performed by the controller device 200. For example, the co-owned U.S. patent application Ser. No. 12/251,629 (published as U.S. Patent Publication No. 2010/0094251), which is hereby incorporated by reference in its entirety, discloses systems and processes for calculation of TIL that are applicable to the present embodiment.

In a third alternative embodiment, the predicted value for the user's future blood glucose level (PBG) can be calculated according to the following algorithm that is executed by the pump controller:

$$PBG=BG+R*T-IOB_{correction}*Si$$

where:
PBG is the predicted blood glucose level;
BG is the blood glucose level at $t_n$;
R is the rate of change of the trend of past blood glucose data points;
T is the time increment into the future that the calculated PBG pertains to;
$IOB_{correction}$ is the bolus insulin-on-board for correction boluses only (excluding meal bolus dosages) at $t_n$ as described above; and
Si is the insulin sensitivity factor.
This third embodiment employs a simplified equation that eliminates the need to calculate or store the FOB. In general, the aforementioned algorithm can focus on the correction-related bolus dosages, and because the food-related bolus dosages (e.g., meal boluses) are not employed in the estimation for the insulin remaining in the user's body that has not yet acted, the FOB component may also not be employed. Such an algorithm can be used to provide a reasonable approximation for the user's predicted blood glucose level without necessarily requiring an analysis of the FOB component.

In a fourth alternative embodiment that is partially similar to the third embodiment described immediately above, the $TIL_{correction}$ estimate can be substituted for $IOB_{correction}$ estimate to result in the predicted value for the user's future blood glucose level (PBG) calculated according to the following algorithm that is executed by the pump controller:

$$PBG=BG+R*T-TIL_{correction}*Si,$$

where:
PBG is the predicted blood glucose level;
BG is the blood glucose level at $t_n$;
R is the rate of change of the trend of past blood glucose data points;
T is the time increment into the future that the calculated PBG pertains to;
$TIL_{correction}$ is the Total Insulin Load at $t_n$ as described above, except that the basal dosages and correction boluses only and included (while meal bolus dosages are excluded);
Si is the insulin sensitivity factor.
Here again, this fourth embodiment employs a simplified equation that eliminates the need to calculate or store the FOB. Because the food-related bolus dosages (e.g., meal boluses) are not employed in the estimation for the $TIL_{correction}$, the FOB component need not be employed in this example. Such an algorithm can be used to provide a reasonable approximation for the user's predicted blood glucose level without necessarily requiring an analysis of the FOB component.

In a fifth alternative embodiment, the predicted value for the user's future blood glucose level (PBG) can be calculated according to the following algorithm that is executed by the pump controller:

$$PBG=BG-IOB*Si+Si*FOB/C,$$

where:
PBG is the predicted blood glucose level;
BG is the blood glucose level at $t_n$;

IOB is the bolus insulin-on-board (IOB) at $t_n$ as described above;
Si is the insulin sensitivity factor;
FOB is the food-on-board at $t_n$ estimate; and
C is the estimated carbohydrate ratio of the FOB.

In this embodiment, the controller device employs a simplified equation that eliminates the use of the blood glucose trend data.

In a sixth alternative embodiment that is partially similar to the fifth embodiment described immediately above, the TIL estimate can be substituted for IOB estimate to result in the predicted value for the user's future blood glucose level (PBG) calculated according to the following algorithm that is executed by the pump controller:

$$PBG=BG-TIL*Si+Si*FOB/C,$$

where:
PBG is the predicted blood glucose level;
BG is the blood glucose level at $t_n$;
TIL is the Total Insulin Load at $t_n$ as described above;
Si is the insulin sensitivity factor;
FOB is the food-on-board at $t_n$ estimate; and
C is the estimated carbohydrate ratio of the FOB.

Here again, in this embodiment, the controller device employs a simplified equation that eliminates the use of the blood glucose trend data.

In a seventh alternative embodiment, the predicted value for the user's future blood glucose level (PBG) can be calculated according to the following algorithm that is executed by the pump controller:

$$PBG=BG-IOB_{correction}*Si,$$

where:
PBG is the predicted blood glucose level;
BG is the blood glucose level at $t_n$;
$IOB_{correction}$ is the bolus insulin-on-board for correction boluses only (excluding meal bolus dosages) at $t_n$ as described above; and
Si is the insulin sensitivity factor.

This seventh embodiment employs a simplified equation that eliminates the use of blood glucose trend data and FOB. As previously described, because the food-related bolus dosages (e.g., meal boluses) are not employed in the estimation for the $IOB_{correction}$, the FOB component need not be employed in this example.

In an eighth alternative embodiment that is partially similar to the seventh embodiment described immediately above, the $TIL_{correction}$ estimate can be substituted for $IOB_{correction}$ estimate to result in the predicted value for the user's future blood glucose level (PBG) calculated according to the following algorithm that is executed by the pump controller:

$$PBG=BG-TIL_{correction}*Si$$

where:
PBG is the predicted blood glucose level;
BG is the blood glucose level at $t_n$;
$TIL_{correction}$ is the Total Insulin Load at $t_n$ as described above, except that the basal dosages and correction boluses only and included (while meal bolus dosages are excluded);
Si is the insulin sensitivity factor.

Here again, in this embodiment, the controller device employs a simplified equation that eliminates the use of the blood glucose trend data and FOB.

Still referring to FIG. 11, at operation 560, the process 500 can make a comparison between the calculated predicted blood glucose (PBG) from operation 550 and a lower threshold level to determine whether the PBG is below the lower threshold level (e.g., is the user's blood glucose level predicted to reach below a safety limit or otherwise predetermined limit). The lower threshold level can be generally considered as an alarm/alert level (as described further below). Although it varies on an individualized basis, generally when a person's blood glucose level falls below, for example 70 mg/dL, he or she may exhibit some symptoms such as shakiness, feeling hungry, headaches, dizziness, and weakness. Below approximately 50 mg/dL, people tend to lose mental functioning including loss of consciousness, and they may slip into a coma. Therefore, in this example, a lower threshold level of 70 mg/dL can be considered to be a reasonable lower threshold level setting. However, the lower threshold level can be adjustable in response, for example, to an individual user's physiology, preferences, and medical advice. So, in this embodiment, operation 560 represents the comparison of the calculated PBG to the user's lower threshold level (e.g., 70 mg/dL in this example).

If operation 560 indicates that the PBG is below the lower threshold level, the process 500 has predicted a potential problem and the process 500 moves on to operation 562. At operation 562, the user is presented with an alarm/alert message that communicates to the user that a future low blood glucose event is predicted, and asks whether the user would like to enter a low glucose recovery mode (see, e.g., the display 222 of FIG. 1). That is, in this embodiment, if the user's calculated PBG level is below the lower threshold level, the controller device 200 can communicate a predicted low blood glucose alarm/alert to the user (e.g., an audible alarm or alert, display of text on the display 222 describing an alarm or alert, a vibratory alarm or alert, another communicative output, or a combination thereof). Optionally, the controller device 200 can also prompt the user to take action to correct the predicted low blood glucose level. In one example, the controller device 200 (via user interface 220) can suggest that the user consume some food to increase their blood glucose level, and can prompt the user to accept, modify, or decline the suggestion. The controller device 200 can also prompt the user to enter information about a meal that the user may have consumed, but forgot to enter into the user interface 220. In another example, the controller device 200 can use a cellular phone network (via Bluetooth connectivity with a nearby cell phone or via a cell phone communication equipment installed in the controller device 200) to call an emergency contact number programmed in the controller device 200.

In addition to alerting the user to the predicted low blood glucose level at operation 562, the user can be prompted to accept or decline the option of initiating a low blood glucose recovery mode. If the user declines to enter the low glucose recovery mode, the process 500 moves to operation 590 which depicts the passage of a defined time increment as described above. For example, if the defined time increment is one minute, the process 500 will be restarted at operation 510 at time $t_{n+1}$ which would be one minute after time $t_n$. If the execution of the process steps 510 through 560 again results in a PBG level below the threshold level, the user could once again be presented with an alarm/alert concerning the predicted low blood glucose level. In that case, the user would receive a second alarm approximately just one minute after declining to enter into the low glucose recovery mode. Some users may consider such frequent alarms to be a nuisance. Therefore, some embodiments may include a feature in which the controller device 200 modifies the alarm timer in response to the user declining to enter the low blood glucose recovery mode. This feature can therefore provide a "snooze" option.

Thus, the user may be provided with the option to "snooze" the predicted low blood glucose alarm by declining to enter the low blood glucose recovery mode while, for example, he or she is taking actions to resolve the alarm circumstances. The settings that control the duration of the "snooze" timer can be modified to reduce the occurrences of repeated nuisance alarms or to increase the occurrence of serious safety alarms. For example, in some embodiments the following formula for determining the recurrence frequency (or "snooze" period) of alarms/alerts can be used:

time to wait=alarm urgency/(threshold level−PBG)

where:
"time to wait" is the calculated period during which alarms/alerts will be automatically suppressed by the controller device 200 "snooze function";
"alarm urgency" is a factor that can be selected that represents how frequently the particular user should be or desires to be reminded of the alarms/alerts;
"threshold level" is the alarm/alert level as described above in regard particularly to operation 560; and
PBG is the calculated predicted blood glucose level as described above.

The "time to wait" formula can be illustrated by the following examples:
time to wait=60/(70−50)=3 minutes
time to wait=150/(70−60)=15 minutes As shown, a lower "alarm urgency" value, and lower PBG values will result in more frequent alarm reminders of a predicted low blood glucose level. The "alarm urgency" value can be adjusted based on the appropriate frequency of alarms for the particular user. The PBG values will also cause more frequent alarm reminders when the PBG values are further below the threshold level. In other words, more serious the PBG events, the more frequent the alarm reminders. In this way, the user is discouraged from ignoring a potentially serious pending low blood glucose event.

In some embodiments, the "time to wait" determination can include "brackets" that establish upper and lower "snooze" time limits that won't be exceed even if the calculation would tend to do so. For example, in some embodiments, "brackets" establishing a minimum of 1 minute and a maximum of 30 minute can be established. In that case, no alarm reminder suppression period would ever be less than 1 minute or more than 30 minutes. Any other appropriate bracket limits can also be used.

If, when presented with the PBG alarm and the option to enter the low glucose recovery mode (at operation 562), the user enters an affirmative response, then the process 500 moves to operation 564 whereat the controller device 200 enters the low glucose recovery mode. The operations of the controller device 200 in the low glucose recovery mode can be configured to alter the predicted path of the user's blood glucose level so that the low blood glucose event is avoided. In one example, the operations in the low glucose recovery mode are described in more detail below in regard to FIG. 14. Optionally, the process 500 can be implemented in a manner that requires the user to confirm the actual blood glucose level using a blood strip reader (as a verification of the level detected by the continuous monitoring device 50) prior to moving to operation 564 whereat the controller device 200 enters the low glucose recovery mode. In such optional embodiments, the controller device 200 may be permitted to enter the low glucose recovery mode if the glucose level detected by the blood strip reader is within a predefined range of the lower threshold level (e.g., if the blood glucose level detected from the blood glucose reader is within 15% of the lower threshold level). In addition, the controller device 200 can prompt the user to confirm that the blood glucose level detected from the blood glucose reader should be used to calibrate the readings from continuous monitoring device 50. Optionally, the process 500 can be similarly implemented in a manner that requires the user to confirm the actual blood glucose level using a blood strip reader (as a verification of the level detected by the continuous monitoring device 50) prior to exiting the low glucose recovery mode.

Figure 14:
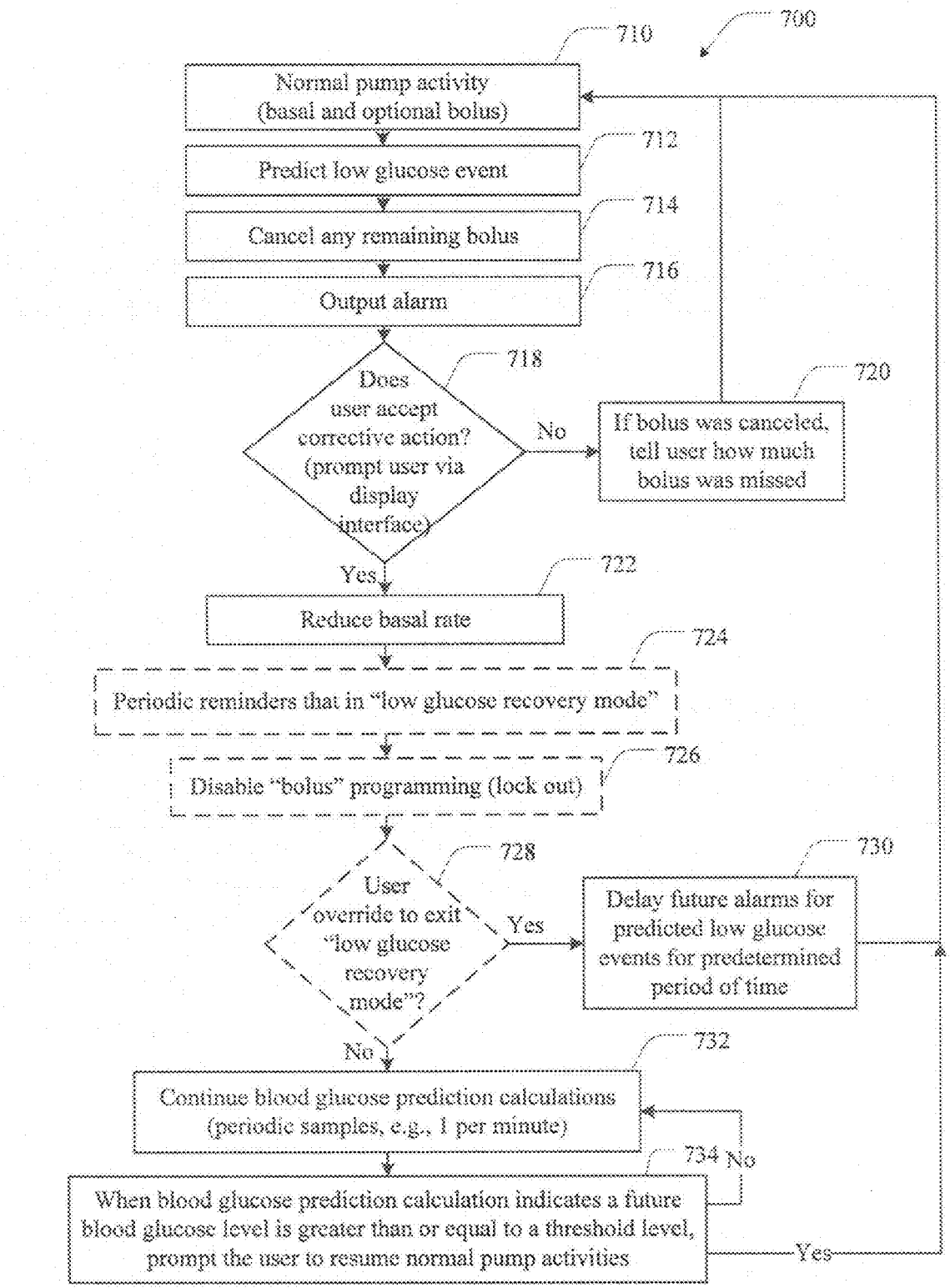
FIG. 14 is a flow diagram depicting an example of a process for operating an insulin infusion pump when a low blood glucose event has been predicted, in accordance with some embodiments.

After the low glucose recovery mode has been initiated, the process 500 can optionally continue to operation 590 (refer also to operation 732 in FIG. 14). At 590, the time period of subsequent PBG calculations is incremented. For example, as described earlier, the process 500 can be setup to repeat on a defined time increment, e.g., every 1 minute, 2 minutes, 5 minutes, 10 minutes, 30 minutes or the like. Operation 590 depicts the expiration of a defined time increment and the initiation of a new point in time for use in a new series of operations beginning at 510 using time $t_n=t_{n+1}$. For example, if the defined time increment is one minute, then one minute after the point in time $t_n$ the process 500 can start over again. Note that the PBG calculations, represented by operations 510 through 560, continue to be performed on a periodic basis even when the controller device 200 has entered into the low blood glucose recovery mode. That way the controller device 200 can track the recovery of the PBG level.

Referring back to operation 560, if the calculated PBG is at or above the lower threshold level, the process 500 may optionally proceed to an operation 570 to make a comparison between the calculated predicted blood glucose (PBG) from operation 550 and an upper threshold level to determine whether the PBG is above the upper threshold level (e.g., is the user's blood glucose level predicted to reach above a safety limit or otherwise predetermined limit?). The upper threshold level can be generally considered as an alarm/alert level (as described further below). Although it varies on an individualized basis, generally when a person's blood glucose level rises above a safe range, he or she may exhibit some symptoms such as excessive urination or thirst and tiredness. In this example, upper threshold level of 200 mg/dL can be considered to be a reasonable upper threshold level setting. However, the lower threshold level can be adjustable in response, for example, to an individual user's physiology, preferences, and medical advice. So, in this embodiment, operation 570 represents the comparison of the calculated PBG to the user's lower threshold level (e.g., 70 mg/dL in this example).

If the PBG is above the upper threshold level, the process 500 has predicted a potential problem and the process 500 moves on to operation 572. At operation 572, the user is presented with an alarm/alert message that communicates to the user that a future high blood glucose event is predicted, and asks whether the user would like to enter a high glucose recovery mode (see, e.g., the display 222 of FIG. 1). That is, in this embodiment, if the user's calculated PBG level is above the upper threshold level, the controller device 200 can communicate a predicted high blood glucose alarm/alert to the user (e.g., an audible alarm or alert, display of text on the display 222 describing an alarm or alert, a vibratory alarm or alert, another communicative output, or a combination thereof).

In addition to alerting the user to the predicted high blood glucose level, the user can be prompted (at operation 572) to accept or decline the option of initiating a high blood glucose recovery mode. If the user declines to enter the low glucose recovery mode, the process 500 moves to operation 590 which depicts the passage of a defined time increment as described above. As previously described, if the defined time increment is one minute, the process 500 will be restarted at operation 510 at time $t_n+1$ which would be one minute after time $t_n$. If the execution of the process steps 510 through 560 again results in a PBG level below the lower threshold level or above the upper threshold level, the user could once again be presented with an alarm/alert concerning the predicted low or high blood glucose level. In that case, the user would receive a second alarm approximately just one minute after declining to enter into the low glucose recovery mode. Some users may consider such frequent alarms to be a nuisance. Therefore, as previously described, some embodiments may include a feature in which the controller device 200 modifies the alarm timer in response to the user declining to enter the low blood glucose recovery mode. This feature can therefore provide a "snooze" option.

If, when presented with the PBG alarm and the option to enter the high glucose recovery mode at operation 572, the user enters an affirmative response, then the process 500 moves to operation 574 whereat the controller device 200 enters the high glucose recovery mode. In the high glucose recovery mode, the process can cause the controller device 200 to prompt the user to take action to correct the predicted high blood glucose level. In one example, the controller device 200 (via user interface 220) can suggest that the user accept a bolus dosage of insulin or to temporarily increase the basal rate of insulin, and can prompt the user to accept, modify, or decline the suggestion. In another example, the controller device 200 can use a cellular phone network (via Bluetooth connectivity with a nearby cell phone or via a cell phone communication equipment installed in the controller device 200) to call an emergency contact number programmed in the controller device 200.

Optionally, the process 500 can be implemented in a manner that requires the user to confirm the actual blood glucose level using a blood strip reader (as a verification of the level detected by the continuous monitoring device 50) prior to moving to operation 574 whereat the controller device 200 enters the high glucose recovery mode. In such optional embodiments, the controller device 200 may be permitted to enter the high glucose recovery mode if the glucose level detected by the blood strip reader is within a predefined range of the upper threshold level (e.g., if the blood glucose level detected from the blood glucose reader is within 15% of the upper threshold level). In addition, the controller device 200 can prompt the user to confirm that the blood glucose level detected from the blood glucose reader should be used to calibrate the readings from continuous monitoring device 50. Optionally, the process 500 can be similarly implemented in a manner that requires the user to confirm the actual blood glucose level using a blood strip reader (as a verification of the level detected by the continuous monitoring device 50) prior to exiting the high glucose recovery mode.

If the calculated PBG from operation 550 is at or above the lower threshold level (operation 560) and is also at or below the upper threshold level (operation 570), no alarm/alert is required, and the process 500 can proceed to operation 580 in which the pump system operates in a normal mode. For example, in normal mode, the pump system can provide the previously programmed basal dosages and permit the user to receive bolus dosages at selected times (e.g., shortly before a meal or the like). When operating in normal mode as indicated by operation 580, the process 500 continues to operation 590 so that the process 500 can repeat itself at another point in time. In other words, if the PBG is at or above the lower threshold level (operation 560) and is also at or below the upper threshold level (operation 570), the process 500 can repeat itself from the beginning after a particular time increment from $t_n$ has expired. The cycle of operations from 510 through 560 can thereby be continuously repeated on a periodic basis while the calculated PBG is within a selected range between the lower threshold level and the upper threshold level. This can be done in the background with generally no need for any user interaction while the pump system operates in the aforementioned normal mode.

The process 500 can be setup to repeat on a defined time increment, e.g., every 1 minute, 2 minutes, 5 minutes, 10 minutes, 30 minutes, or the like. Operation 590 depicts the expiration of the defined time increment. For example, if the defined time increment is one minute, then one minute after $t_n$ the process can start over again (indicated in operation 590 as time $t_n=t_{n+1}$).

Referring now to FIG. 12, in some embodiments, the controller device 200 can calculate the IOB information (refer, for example, to operation 530 in FIG. 11) using, at least in part, time-based models derived from pharmacodynamic data. As previously described, the IOB value of a user can include a bolus insulin load amount which may be determined using a time-decay model generated from pharmacodynamic data associated with the insulin stored in the cartridge 120. As shown by way of example in FIG. 12, the controller device 200 can utilize a time-decay curve (represented by curve 450), which is generated from pharmacodynamic data, to estimate the percentage of insulin remaining in a user's body after a particular period of time. It should be understood that the controller device 200 can be configured to utilize any one of a number of selectable time-decay curves (only one of which is depicted in FIG. 12 as curve 450) for purposes of estimating the percentage of insulin remaining in a user's body after a particular period of time. For example, the various time-decay curves that could be selected during programming of the controller device 200 for a particular user may include: curves with greater or smaller durations, linear approximations of the curve 450 shown in FIG. 12 or other similar curves, hybrid curves having a curve similar to curve 450 in a first region and then followed by a linear decay in a second region, or a customized linear approximation where the user or another person qualified to program the controller device 200 selects the slope (e.g., the rate of decay), the overall time of consumption, or the like.

Figure 13:
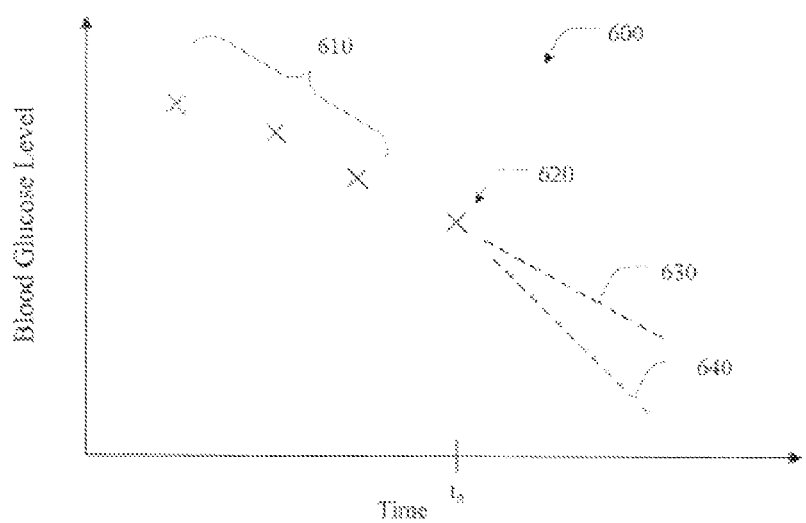
FIG. 13 is a diagram depicting an example of a user's blood glucose level trend, in accordance with some embodiments.

Referring now to FIG. 13, a graph exemplifying a user's blood glucose levels as a function of time 600 is shown. In general, the graph includes past trend data of blood glucose readings 610, a blood glucose reading at current time $t_n$ 620, and two example predicted blood glucose trends 630 and 640. This example of a user's past, present, and predicted blood glucose levels will be used to illustrate some of the benefits of including IOB and FOB (optionally) in a predictive blood glucose algorithm.

The past trend data of blood glucose readings 610 depicts the user as having a declining trend pattern of past blood glucose levels. A curve can be fit to the data 610 in order to help predict what the user's future blood glucose levels will be. For example, the past trend data 610 may indicate that the user's blood glucose level is declining at an average rate of −2 mg/dL per minute (as in the example calculation above). Knowing the past rate of decline, and combining it with a current blood glucose level can enable a prediction of future blood glucose levels.

A current (at time $t_n$) blood glucose level 620, represents the user's current blood glucose level. The graph depicts the current blood glucose level 620 as approximately continuing the trend of falling blood glucose levels to an extent that is similar to the pattern of past trend data 610. Therefore, one could expect that the trend of declining blood glucose levels would continue to decline at approximately the same rate in the future beyond time $t_n$. For example, if the user's blood glucose levels depicted by past trend data 610 and current level 620 are declining at an average rate of −2 mg/dL per minute, one could expect that in one minute after $t_n$ the user's blood glucose level will become 2 mg/dL less than the current blood glucose level 620. Extending this example further, one could expect that in two minutes after $t_n$ the user's blood glucose level will become 4 mg/dL less that the current blood glucose level 620, and so on.

The first predictive trend line 630 depicts an expected trend of future blood glucose levels based solely on the past trend data 610 and the current blood glucose level 620 at time $t_n$. As shown, the slope of the first predictive trend line 630 is similar to the slope of a line that would represent the past trend data 610 and current level 620. Using the first predictive trend line 630 the user's future blood glucose levels can be predicted and compared to a threshold level to determine whether to initiate an alarm. For example, as described in reference to FIG. 11, if a future blood glucose level on the first predictive trend line 630 is below the lower threshold level, the user can be presented with an alarm and prompt the user to indicate whether the user would like to enter a low glucose recovery mode.

As described above, in some embodiments, including an IOB component in a blood glucose prediction can improve the accuracy of future blood glucose predictions. To illustrate that, a second predictive trend line 640 is provided that represents an expected trend of future blood glucose levels based on the past trend 610, the current level 620, and an estimate of the user's IOB at time $t_n$. As described in reference to FIG. 12, some types of insulin can take hours to fully take effect in a user's body. Therefore, a recently infused bolus of insulin can be expected to have a future downward influence on the user's blood glucose levels—and the influence may not be fully captured in the past trend data 610. In such a case, the second predictive trend line 640 (which accounts for the influence of IOB) may provide a more accurate prediction of the user's future blood glucose levels than would the first predictive trend line 630 (which does not necessarily account for the impact of IOB on the user's future blood glucose levels). When the second predictive trend line 640 is compared to a blood glucose threshold level, it may provide a different result than when the first predictive trend line 630 is compared to the threshold level. For example, as shown in FIG. 13, the second predictive trend line 640 is lower than the first predictive trend line 630. In some cases, the second predictive trend line 640 may be below the lower blood glucose threshold level while the first predictive trend line 630 is not below the lower threshold level. In that example scenario, the pump controller device 200 would provide a predicted low blood glucose alarm when the algorithm includes the influence of IOB, but not when the algorithm excludes the influence of IOB. Thus, a pump controller device 200 that predicts the user's future blood glucose level by accounting for the influence of IOB can increase the accuracy of the prediction, and the pump controller device 200 could, in some circumstances, provide an alarm to the user that might not otherwise be provided if the controller device 200 did not account for the influence of IOB on the predicted blood glucose value.

Referring now to FIG. 14, some embodiments of a process 700 for operating an insulin infusion pump can be used by an infusion pump system to initiate a "low glucose recovery mode" when a future low blood glucose event has been predicted. In this embodiment, the process 700 may begin at operation 710 which depicts the normal activity of the infusion pump system 10. The normal activity can include delivering to the user scheduled basal dosages of insulin (or other medication) along with user-selected bolus dosages. The basal rate can be selected to maintain a user's blood glucose level in a target range during normal activity when the user is not eating or otherwise consuming food items. The selected bolus deliveries may provide substantially larger amounts of insulin to limit the blood glucose level during certain circumstances, such as the consumption of carbohydrates and other food items.

At operation 712, the pump controller device 200 can predict a low glucose event that may occur in the near future. For example, the calculate a predicted blood glucose level (as described in detail above in in connection with FIG. 11) that is below a lower threshold level, thereby indicating that the user's blood glucose level is on a path to fall below the lower threshold level. In some embodiments, as described above, the trend of past blood glucose data and the user's most recent blood glucose level can be employed to calculate a predicted blood glucose level. As described above, an IOB estimation or a TIL estimation can be included in the calculation in order to enhance the accuracy of the blood glucose prediction. Optionally, a food-on-board (FOB) estimation can also be included in the calculation in order to possibly enhance the accuracy of the predicted blood glucose value at a future point in time. Operation 712 in FIG. 14 is depicted as having predicted a low blood glucose event. Therefore, the subsequent operations of process 700 take place as a result of this low blood glucose prediction at operation 712.

Optionally, the process 700 can be implemented in a manner that requires the user to confirm the actual blood glucose level using a blood strip reader (as a verification of the level detected by the continuous monitoring device 50) prior to moving to the subsequent operations in which the controller device 200 enters the low glucose recovery mode. As previously described, in such optional embodiments, the controller device 200 may be permitted to enter the low glucose recovery mode if the glucose level detected by the blood strip reader is within a predefined range of the lower threshold level (e.g., if the blood glucose level detected from the blood glucose reader is within 15% of the lower threshold level).

When the infusion pump system predicts that a low glucose level will occur in the near future, the pump controller can be configured to initiate or suggest one or more countermeasures in response. A number of countermeasures are described herein in connection with process 700.

For example, the process 700 may optionally include operation 714, which causes the immediate cancelation any remaining bolus dosage that has not yet dispensed to the user. In general, the user may select one or more bolus deliveries, for example, to offset the blood glucose effects caused by the intake of food. The bolus dosages can be dispensed over time in user-selected amounts based on calculations made by the controller device 200 in response, for example, to an indication from the user of how many carbohydrates they plan to consume. In some embodiments, the entire bolus amount may not be infused within a short time frame (e.g., within minutes). Rather, infusion of the bolus amount may be spread over a greater period of time (e.g., a period of an hour or more in some circumstances). Operation 714 depicts a scenario where a low blood glucose event is predicted during a period of time over which a bolus amount is being infused. In such a scenario, the controller device 200 can cancel any remaining bolus amount—in order to prevent causing the user's blood glucose level, which is already predicted to fall too low, from being driven further lower still. IN some embodiments, the operation 714 may be performed automatically (without user input) after infusion pump system predicts that a low glucose level will occur in the near future. Alternatively, this operation 714 may be performed only after confirming that the user accepts this countermeasure (e.g., only after receiving user input) in response to the infusion pump system predicting that a low glucose level will occur in the near future.

At operation 716, the controller device 200 can output an alarm in association with the predicted low blood glucose event. For example, the user can be presented with an alarm/alert message that communicates to the user that a future low blood glucose event is predicted, and that asks whether the user would like to enter a low glucose recovery mode (see, e.g., the display 222 of FIG. 1). That is, the controller device 200 can communicate a predicted low blood glucose alarm/alert to the user (e.g., an audible alarm or alert, display of text on the display 222 describing an alarm or alert, a vibratory alarm or alert, another communicative output, or a combination thereof). Optionally, the controller device 200 can also prompt the user to take remedial action to correct the predicted low blood glucose level. In one example, the controller device 200 (via user interface 220) can suggest that the user consume some food to increase their blood glucose level, and can prompt the user to accept, modify, or decline the suggestion. The controller device 200 can also prompt the user to enter information about a meal that the user may have consumed, but forgot to enter into the user interface 220. In another example, the controller device 200 can use a cellular phone network (for example, via Bluetooth connectivity with a nearby cell phone or via a cell phone communication equipment installed in the controller device 200) to call an emergency contact number programmed in the controller device 200.

In addition to alerting the user to the predicted low blood glucose level at operation 716, the pump controller can prompt the user to accept or decline the corrective action of initiating a low blood glucose recovery mode, as indicated at operation 718. In some alternative embodiments, in addition to the "yes" and "no" input options from the user associated with operation 718, the user may also choose to "snooze" the alarm (as described in connection with FIG. 11 above) to thereby postpone their decision, and to be presented with the prompt again after a period of time.

If the pump controller receives user input indicating that the user declines to accept the corrective action of entering the low glucose recovery mode, the process 700 moves to operation 720. At operation 720, if some amount of a bolus was not yet infused and canceled at operation 714 the user is informed via the user interface 220 how much bolus was missed. In such a case, the user may choose to take actions to make up for the canceled bolus amount. After presenting the missed bolus information to the user, the controller device 200 can return the infusion pump system 10 back to the normal pump activity at operation 710.

If the user accepts the corrective action of entering the low glucose recovery mode, the process 700 advances to operation 722. At operation 722, the basal rate of the pump device 100 is reduced. It is desirable to reduce the basal rate because the infusion of additional insulin will tend to slow the recovery rate of the user's low blood glucose level. But, in some circumstances, it can be more desirable to continue to provide a low basal flow rate rather than to completely stop the flow. For example, completely stopping the basal flow may contribute to clogs in the infusion line, whereas the continuation of a minimal flow level can reduce the likelihood of such problems.

At operation 724, the controller device 200 can optionally provide periodic reminders to the user via the user interface 220 that the infusion pump system 10 is in the lower glucose recovery mode. The reminders can include textual messages and/or icons displayed on the user interface 220. Audible or vibratory indications can be provided in some embodiments too. The periodic reminders may, in some embodiments, also include the display of a textual prompt on the user interface 220 to treat the low glucose level by consuming food. In some embodiments, the reminders can be provided periodically on a basis of about every 5-20 minutes. The reminders can also include an indication of an updated predicted blood glucose level so that the user can be aware of the progress of their recovery from their low, or predicted low, blood glucose status.

At operation 726, the process 700 can optionally disable the bolus programming function of the infusion pump system 10. Disablement (lock-out) of the bolus programming function when the user is in the low blood glucose recovery mode can be desirable because the infusion of additional insulin would likely be counter-productive to the user's efforts to maintain a blood glucose level in a safe range. Therefore, such an optional safety feature can be provided in some embodiments to prevent bolus infusions while the pump system 10 is in the low blood glucose recovery mode. For example, in response to a user's attempt to program a bolus delivery while the pump system 10 is in the low blood glucose recovery mode, the user interface 220 may display a message along the lines of: "No bolus allowed—glucose recovery mode in effect."

At operation 728, the pump controller can optionally provide the user with an option to manually override and exit the low glucose recovery mode. For example, the user can, in some embodiments, be provided with an ability to manually exit the low glucose recovery mode by making a particular menu selections using buttons 224a-d.

If the user chooses to manually exit the low blood glucose recovery mode, the process 700 advances to operation 730. At operation 730, the infusion pump system 10 has exited the low glucose recovery mode and future alarms for predicted low glucose events can be suspended for a period of time. In some embodiments, the period of time that the alarms are suspended for can be determined in part based on the seriousness the user's low, or predicted low, blood glucose condition.

After operation 730, the process 700 can advance to operation 710 for normal pump activity. However, in some embodiments, controller device 200 can be programed to delay the resumption of normal operations of the pump system 10 when the user has manually exited the low glucose recovery mode. In some embodiments, the duration of the delay of resuming normal pump activity can depend in part on the seriousness of the user's low, or predicted low, blood glucose condition.

If the user does not manually exit the low blood glucose recovery mode, the infusion pump system 10 can continue in the low blood glucose recovery mode, and the process 700 can advance to operation 732. At operation 732 the controller device 200 can continue to make blood glucose prediction calculations on a periodic basis. For example, in some embodiments, operation 732 can generally be performed in the manner and on a periodic time basis that is the same as or substantially similar to the process 500 described above in reference to FIG. 11. The predictive calculations can be based on the blood glucose trend data, current blood glucose level, the IOB estimate (or the TIL estimate), and optionally the FOB estimate, as with process 500. The calculations can be performed on a periodic basis, e.g., every 1 minute, 2 minutes, 5 minutes, and so on, as described above.

At operation 734, the calculated blood glucose prediction can be compared to a threshold level to determine whether the infusion pump system 10 should continue in the low blood glucose recovery mode or whether the infusion pump system 10 should exit from the low blood glucose recovery mode to return to the normal mode. For example, when the calculated predicted blood glucose level is below the threshold level, the process 700 can remain in the low blood glucose recovery mode and can return to operation 732. In contrast, when the calculated predicted blood glucose level is above the threshold level, the process 700 can automatically (without manual intervention from the user) exit the low blood glucose recovery mode and can return to the normal pump activity mode at operation 710. In such circumstances, the user interface may notify the user (e.g., via the display device) that the low glucose recovery mode was successful and the pump system has returned to a normal operation mode. Optionally, the process 700 can be implemented in a manner that requires the user to confirm the actual blood glucose level using a blood strip reader (as a verification of the level detected by the continuous monitoring device 50) prior to exiting the low glucose recovery mode and return to the normal pump activity mode at operation 710.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
a portable pump housing that receives insulin for dispensation to a user, the pump housing at least partially containing a pump drive system to dispense the insulin through a flow path to the user;
a controller that communicates with the pump drive system to dispense the insulin from the portable pump housing; and
a monitoring device that communicates glucose information to the controller, the glucose information being indicative of a blood glucose level of the user, wherein the controller is configured to: predict a future blood glucose level of the user based at least in part upon a recent blood glucose level, a trend of blood glucose levels over time, and an insulin load of the user, operate in a low glucose recovery mode in which a basal rate is reduced as compared to a normal operational mode in response to the predicted future blood glucose level being less than a lower threshold value, and in response to the activation of the controller to operate in the low glucose recovery mode, automatically exit from the low glucose recovery mode and return to the normal operational mode based on a subsequent determination that the predicted future blood glucose level is greater than or equal to the lower threshold value, wherein the controller is further configured to operate in a high glucose recovery mode in which a basal rate is temporarily increased in response to the predicted future blood glucose level being greater than an upper threshold level; and
wherein in response to the controller calculating the predicted future blood glucose level being less than the lower threshold value, the controller automatically cancels any previously scheduled bolus amount of insulin to be dispensed from the portable pump housing and informs the user of how much bolus was missed.

2. The system of claim 1, wherein the controller calculates the predicted future blood glucose level of the user based at least in part upon the recent blood glucose level, the trend of blood glucose levels over time, and the insulin load of the user, the insulin load of the user being an estimated value of previously dispensed insulin that has not yet acted in the user.

3. The system of claim 2, wherein the insulin load is an insulin-on-board estimate indicative of bolus insulin dosages that have been dispensed but not yet acted in the user.

4. The system of claim 2, wherein the insulin load is total-insulin-load estimate indicative of both bolus and basal insulin dosages that have been dispensed but not yet acted in the user.

5. The system of claim 1, wherein the controller calculates the predicted future blood glucose level of the user based at least in part upon the recent blood glucose level, the trend of blood glucose levels over time, the insulin load of the user, and a food-on-board value, the food-on-board value being indicative of previous food intake by the user that has not yet metabolized in the user.

6. The system of claim 1, further comprising one or more computer-readable memory device of the controller that store the glucose information received from the monitoring device and time values associated with the glucose information.

7. The system of claim 6, wherein the one or more computer-readable memory devices of the controller store computer-readable instructions for a blood glucose prediction process that, when executed by a processor of the controller, cause the controller to:
calculate the predicted future blood glucose level of the user based at least in part upon the recent blood glucose level, the trend of blood glucose levels over time, and the insulin load of the user;
output an alarm in response to the predicted future blood glucose level being less than the lower threshold value; and
operate in the low glucose recovery mode in response to user input that confirms an operational change for the controller.

8. The system of claim 1, further comprising a user interface coupled to the controller, the user interface including (i) a display device that is configured to provide a visual indication of an alarm and (ii) a user input device that is configured to receive user input to activate the controller to operate in the low glucose recovery mode.

9. The system of claim 8, wherein in response to the activation of the controller to operate in the low glucose recovery mode, the controller communicates with the pump drive system to reduce, but not stop, a basal rate amount of insulin to be dispensed the from the portable pump housing.

10. The system of claim 1, wherein the controller comprises a controller housing that removably attaches to the pump housing, the controller being electrically connected to the pump drive system when the controller housing is removably attached to the pump housing, wherein the controller is a reusable device while at least one of the pump housing and the pump drive system include a structure to prevent reuse of the pump housing and the pump drive system.

11. The system of claim 1, wherein the portable pump housing defines an opening that slidably receives a prefilled cartridge of the insulin, further comprising a cap device configured to cover the opening and pierce the prefilled cartridge of insulin when the portable pump housing receives the prefilled cartridge of insulin.

12. The system of claim 1, wherein the monitoring device comprises a portable housing wearable on the user's skin, a sensor shaft that penetrates into the user's skin, and a wireless communication device to transmit the glucose information to a wireless communication device of the controller.

13. A controller for an insulin infusion pump system, comprising:
  a processor;
  one or more computer-readable memory devices that store glucose information received from a monitoring device and time values associated with the glucose information, wherein the one or more computer-readable memory devices store computer-readable instructions for a blood glucose prediction process that, when executed by the processor, cause the controller to:
  calculate a predicted future blood glucose level of the user based at least in part upon a recent blood glucose level of a user, a trend of blood glucose levels over time, and an insulin load of the user;
  output an alarm in response to the predicted future blood glucose level being less than a lower threshold value; and
  operate in a low glucose recovery mode in response to user input that accepts activation of the low glucose recovery mode; and
  in response to the activation of the controller to operate in the low glucose recovery mode, automatically exit from the low glucose recovery mode based on a subsequent determination that the predicted future blood glucose level is greater than or equal to the lower threshold value and return to a normal operational mode;
  wherein a basal rate is reduced in the low glucose recovery mode as compared to the normal operational mode;
  wherein a previously scheduled bolus amount of insulin is canceled in the low glucose recovery mode and the alarm informs the user of how much bolus was missed; and
  output an alarm in response to the predicted future blood glucose level being greater than an upper threshold level; and
  operate in a high glucose recovery mode in response to user input that accepts activation of the high glucose recovery mode, wherein a basal rate is temporarily increased in the high glucose recovery mode as compared to the normal operational mode.

14. The controller of claim 13, wherein the one or more computer-readable memory devices store computer-readable instructions for the blood glucose prediction process that, when executed by the processor, cause the controller to:
  in response to the activation of the controller to operate in the low glucose recovery mode, reduce but not stop a basal rate amount of insulin to be dispensed while operating in the low glucose recovery mode.

15. A method of operating an insulin infusion pump system, comprising:
  receiving, at a controller of an insulin infusion pump system, glucose information indicative of a glucose level of a user;
  determining an insulin load value indicative of an estimated value of previously dispensed insulin that has not yet acted in the user;
  calculating, at the controller of the insulin infusion pump system, a predicted future blood glucose level of the user based at least in part upon a recent glucose level of the user, a trend of blood glucose levels over time, and the insulin load of the user;
  in response to the predicted future blood glucose level being less than a lower threshold value or greater than a higher threshold value, outputting an alarm from the insulin infusion pump system;
  operating in a low glucose recovery mode in which a basal rate is reduced as compared to a normal operational mode in response to the predicted future blood glucose level being less than a lower threshold value; and
  automatically exiting from the low glucose recovery mode and returning to the normal operational mode based on a subsequent determination that the predicted future blood glucose level is greater than or equal to the lower threshold value, in response to the activation of the controller to operate in the low glucose recovery mode; and
  canceling any previously scheduled bolus amount of insulin to be dispensed from the portable pump housing and informing the user of how much bolus was missed in response to the controller calculating the predicted future blood glucose level being less than the lower threshold value;
  operating in a high glucose recovery mode in which a basal rate is temporarily increased as compared to a normal operational mode in response to the predicted future blood glucose level being greater than an upper threshold level.

16. The method of claim 15, further comprising, in response to the predicted future blood glucose level being less than the lower threshold value or greater than the higher threshold value, prompting the user to confirm a change to an operational mode of the insulin infusion pump system.

17. The method of claim 16, further comprising, in response to the predicted future blood glucose level being less than the lower threshold value, prompting the user to confirm activation of the low glucose recovery mode for the insulin infusion pump system.

18. The method of claim 15, further comprising, in response to the predicted future blood glucose level being less than the lower threshold value, stopping any previously scheduled bolus amount of insulin to be dispensed from the insulin infusion pump system.

19. The method of claim 15, wherein, the determined predicted future blood glucose level is further based on a food on board component, in addition to the glucose information and the dispensed insulin amount, and wherein the food on board component is based on previous food intake by the user that has not yet metabolized in the user.

20. The method of claim 15, further comprising activating a pump drive system of the insulin infusion pump system to dispense the insulin through a flow path.

21. The method of claim 15, wherein receiving the glucose information comprises receiving at the controller of the insulin infusion pump system a wireless signal from a wireless glucose monitoring device wearable on the user's body.

22. A method of operating an insulin infusion pump system, comprising:
   receiving, at a controller of an insulin infusion pump system, glucose information indicative of a glucose level of a user;
   determining an insulin load value indicative of an estimated value of previously dispensed insulin that has not yet acted in the user;
   calculating, at the controller of the insulin infusion pump system, a predicted future blood glucose level of the user based at least in part upon a recent glucose level of the user, a trend of blood glucose levels over time, and the insulin load of the user; and
   in response to the predicted future blood glucose level being less than a lower threshold value or greater than a higher threshold value, outputting an alarm from the insulin infusion pump system;
   further comprising, in response to the predicted future blood glucose level being less than the lower threshold value, prompting the user to confirm activation of a low glucose recovery mode for the insulin infusion pump system;
   wherein in response to user input confirming the activation of the low glucose recovery mode for the insulin infusion pump system, the method further comprises:
   reducing but not stopping a basal rate amount of insulin to be dispensed from the insulin infusion pump system;
   canceling any previously scheduled bolus amount of insulin to be dispensed from the portable pump housing in response to the controller calculating the predicted future blood glucose level being less than the lower threshold value and informing the user of how much bolus was missed
   subsequently predicting the future blood glucose level of the user based upon updated glucose information indicative of the glucose level of a user, an updated trend of blood glucose levels over time, and an updated insulin load of the user; and
   activating the insulin infusion pump system to return to a normal operational mode in response to the subsequently predicted future blood glucose level being greater than or equal to the lower threshold level; and
   operating in a high glucose recovery mode in which a basal rate is temporarily increased as compared to a normal operational mode in response to the predicted future blood glucose level being greater than an upper threshold level.

23. The method of claim 22, wherein a bolus programming function is disabled during the low glucose recovery mode.

\* \* \* \* \*